United States Patent
Lundquist et al.

(10) Patent No.: US 7,961,314 B2
(45) Date of Patent: Jun. 14, 2011

(54) METHODS AND SYSTEMS FOR SIMULTANEOUS REAL-TIME MONITORING OF OPTICAL SIGNALS FROM MULTIPLE SOURCES

(75) Inventors: Paul Lundquist, San Jose, CA (US); Denis Zaccarin, San Jose, CA (US); Yves Lacroix, San Jose, CA (US); Stephen Turner, Menlo Park, CA (US); John Dixon, Moss Beach, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 454 days.

(21) Appl. No.: 11/978,211

(22) Filed: Oct. 26, 2007

(65) Prior Publication Data
US 2008/0157005 A1    Jul. 3, 2008

Related U.S. Application Data

(63) Continuation of application No. 11/704,733, filed on Feb. 9, 2007, which is a continuation-in-part of application No. 11/483,413, filed on Jul. 7, 2006.

(60) Provisional application No. 60/772,908, filed on Feb. 13, 2006.

(51) Int. Cl.
*G01J 3/30* (2006.01)
(52) U.S. Cl. ................................................... 356/317
(58) Field of Classification Search .................. 356/317; 250/458.1
See application file for complete search history.

(56) References Cited

U.S. PATENT DOCUMENTS

| | | | |
|---|---|---|---|
| 4,626,684 A | 12/1986 | Landa | |
| 5,239,178 A | 8/1993 | Derndinger et al. | |
| 5,470,710 A | 11/1995 | Weiss et al. | |
| 5,545,531 A | 8/1996 | Rava et al. | |
| 5,547,839 A | 8/1996 | Dower et al. | |
| 5,578,832 A | 11/1996 | Trulson et al. | |
| 5,631,734 A | 5/1997 | Stern et al. | |
| 5,677,196 A | 10/1997 | Herron et al. | |
| 5,695,934 A | 12/1997 | Brenner | |
| 5,744,305 A | 4/1998 | Fodor et al. | |
| 5,817,462 A | 10/1998 | Garini et al. | |
| 5,821,058 A | 10/1998 | Smith et al. | |
| 5,837,858 A * | 11/1998 | Brennan | 536/25.3 |

(Continued)

FOREIGN PATENT DOCUMENTS
EP    1105529 B1    11/2005
(Continued)

OTHER PUBLICATIONS

M.J. Levene, et al. (Jan. 31, 2003) "Zero-mode Waveguides for Single-molecule Analysis at High Concentrations." Science, 299: 682-686.

(Continued)

*Primary Examiner* — Kara E Geisel
(74) *Attorney, Agent, or Firm* — Robert H. Reamey

(57) ABSTRACT

Methods and systems for real-time monitoring of optical signals from arrays of signal sources, and particularly optical signal sources that have spectrally different signal components. Systems include signal source arrays in optical communication with optical trains that direct excitation radiation to and emitted signals from such arrays and image the signals onto detector arrays, from which such signals may be subjected to additional processing.

20 Claims, 17 Drawing Sheets

U.S. PATENT DOCUMENTS

| | | | |
|---|---|---|---|
| 5,874,219 A * | 2/1999 | Rava et al. | 435/6 |
| 6,071,748 A | 6/2000 | Modlin et al. | |
| 6,160,618 A | 12/2000 | Garner | |
| 6,210,896 B1 | 4/2001 | Chan | |
| 6,236,945 B1 | 5/2001 | Simpson et al. | |
| 6,263,286 B1 | 7/2001 | Gilmanshin et al. | |
| 6,388,788 B1 | 5/2002 | Harris et al. | |
| 6,403,970 B1 * | 6/2002 | Hung | 356/317 |
| 6,455,861 B1 * | 9/2002 | Hoyt | 356/318 |
| 6,597,450 B1 * | 7/2003 | Andrews et al. | 356/317 |
| 6,603,537 B1 | 8/2003 | Dietz et al. | |
| 6,686,582 B1 * | 2/2004 | Volcker et al. | 250/461.2 |
| 6,690,002 B2 | 2/2004 | Kuroda et al. | |
| 6,699,655 B2 | 3/2004 | Nikiforov | |
| 6,760,105 B2 | 7/2004 | Oshida et al. | |
| 6,784,982 B1 | 8/2004 | Blumenfeld et al. | |
| 6,800,860 B2 | 10/2004 | Dietz et al. | |
| 6,818,395 B1 | 11/2004 | Quake et al. | |
| 6,867,851 B2 | 3/2005 | Blumenfeld et al. | |
| 6,869,764 B2 | 3/2005 | Williams et al. | |
| 6,917,726 B2 | 7/2005 | Levene et al. | |
| 6,919,211 B1 | 7/2005 | Fodor et al. | |
| 6,979,830 B2 | 12/2005 | Dietz et al. | |
| 6,982,146 B1 | 1/2006 | Schneider et al. | |
| 7,008,766 B1 | 3/2006 | Densham | |
| 7,033,762 B2 | 4/2006 | Nelson et al. | |
| 7,033,764 B2 | 4/2006 | Korlach et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,064,197 B1 | 6/2006 | Rabbani et al. | |
| 7,081,954 B2 | 7/2006 | Sandstrom | |
| 7,083,914 B2 | 8/2006 | Seul et al. | |
| 7,130,041 B2 | 10/2006 | Bouzid et al. | |
| 7,135,667 B2 | 11/2006 | Oldham et al. | |
| 7,139,074 B2 | 11/2006 | Reel | |
| 7,145,645 B2 | 12/2006 | Blumenfeld et al. | |
| 7,170,597 B1 * | 1/2007 | Hooper et al. | 356/317 |
| 7,189,361 B2 | 3/2007 | Carson et al. | |
| 7,199,357 B1 | 4/2007 | Oldham et al. | |
| 7,209,836 B1 | 4/2007 | Schermer et al. | |
| 7,227,128 B2 | 6/2007 | Sagatelyan | |
| 7,233,393 B2 | 6/2007 | Tomaney et al. | |
| 7,292,742 B2 | 11/2007 | Levene et al. | |
| 7,302,146 B2 * | 11/2007 | Turner et al. | 356/38 |
| 7,302,348 B2 | 11/2007 | Ghosh et al. | |
| 7,323,681 B1 | 1/2008 | Oldham et al. | |
| 2001/0033374 A1 * | 10/2001 | Hoyt | 356/317 |
| 2001/0046050 A1 | 11/2001 | Hoyt | |
| 2002/0008148 A1 | 1/2002 | Empedocles et al. | |
| 2003/0044781 A1 | 3/2003 | Korlach et al. | |
| 2003/0077610 A1 | 4/2003 | Nelson et al. | |
| 2003/0087282 A1 * | 5/2003 | Oshida et al. | 356/319 |
| 2003/0103207 A1 | 6/2003 | Kopf-Sill et al. | |
| 2003/0112432 A1 * | 6/2003 | Yguerabide et al. | 356/317 |
| 2003/0151735 A1 | 8/2003 | Blumenfeld et al. | |
| 2003/0174324 A1 | 9/2003 | Sandstrom | |
| 2003/0174992 A1 | 9/2003 | Levene et al. | |
| 2003/0175987 A1 | 9/2003 | Verdonk et al. | |
| 2003/0186276 A1 | 10/2003 | Odedra | |
| 2003/0190647 A1 | 10/2003 | Odera | |
| 2003/0194740 A1 | 10/2003 | Williams | |
| 2003/0215862 A1 | 11/2003 | Parce et al. | |
| 2004/0038390 A1 * | 2/2004 | Boege et al. | 435/288.7 |
| 2004/0048301 A1 | 3/2004 | Sood et al. | |
| 2004/0197816 A1 | 10/2004 | Empedocles et al. | |
| 2004/0224319 A1 | 11/2004 | Sood et al. | |
| 2005/0135974 A1 | 6/2005 | Harvey et al. | |
| 2005/0206895 A1 | 9/2005 | Salmelainen | |
| 2006/0007439 A1 | 1/2006 | Corcoran | |
| 2006/0040379 A1 * | 2/2006 | Tanaami | 435/287.2 |
| 2006/0152727 A1 * | 7/2006 | Bickmore et al. | 356/417 |
| 2007/0048748 A1 | 3/2007 | Williams et al. | |
| 2007/0099212 A1 | 5/2007 | Harris | |
| 2007/0114362 A1 * | 5/2007 | Feng et al. | 250/458.1 |
| 2008/0020938 A1 | 1/2008 | Kaplan | |

FOREIGN PATENT DOCUMENTS

| | | |
|---|---|---|
| WO | WO 91/06678 | 5/1991 |
| WO | WO 96/27025 | 9/1996 |
| WO | WO 99/05315 | 2/1999 |
| WO | WO 00/36152 | 6/2000 |
| WO | WO 01/16375 A2 | 3/2001 |
| WO | WO 2004/100068 A2 | 11/2004 |
| WO | WO 2006/116726 A2 | 2/2006 |
| WO | WO 2006/135782 A2 | 12/2006 |
| WO | WO 2007/002367 A2 | 1/2007 |
| WO | WO 2007/011549 A1 | 1/2007 |
| WO | WO 2008/002765 A2 | 1/2008 |

OTHER PUBLICATIONS

International Search Report and Written Opinion dated Mar 17, 2008 for related foreign case PCT/US2007/003804.

International Preliminary Report on Patentability dated Aug. 28, 2008 for related foreign case PCT/US2007/003804.

Office Action dated Jan. 8, 2010 for related CN case 200780013250.7.

Office Action dated Jun. 24, 2010 or related CN case 200780013250.7.

International Search Report and Written Opinion dated Feb. 22, 2008 for related foreign case PCT/US2007/003570.

International Preliminary Report on Patentability dated Aug. 28, 2008 for related foreign case PCT/US2007/003570.

* cited by examiner

US 7,961,314 B2

METHODS AND SYSTEMS FOR SIMULTANEOUS REAL-TIME MONITORING OF OPTICAL SIGNALS FROM MULTIPLE SOURCES

CROSS-REFERENCE TO RELATED APPLICATIONS

This application is a continuation of U.S. patent application Ser. No. 11/704,733 filed Feb. 9, 2007 which claims priority from Provisional U.S. Patent Application 60/772,908, filed Feb. 13, 2006, and which is a continuation-in-part of U.S. patent application Ser. No. 11/483,413, filed Jul. 7, 2006, the full disclosures of each of which are hereby incorporated herein by reference in their entirety for all purposes.

STATEMENT REGARDING FEDERALLY SPONSORED RESEARCH

Portions of this invention were made under NHGRI Grant No. R01 HG003710-01, and the government may have rights to such inventions.

BACKGROUND OF THE INVENTION

Optical detection systems are generally employed in a wide variety of different analytical operations. For example, simple multi-well plate readers have been ubiquitously employed in analyzing optical signals from fluid based reactions that were being carried out in the various wells of a multiwell plate. These readers generally monitor the fluorescence, luminescence or chromogenic response of the reaction solution that results from a given reaction in each of 96, 384 or 1536 different wells of the multiwell plate.

Other optical detection systems have been developed and widely used in the analysis of analytes in other configurations, such as in flowing systems, i.e., in the capillary electrophoretic separation of molecular species. Typically, these systems have included a fluorescence detection system that directs an excitation light source, e.g., a laser or laser diode, at the capillary, and is capable of detecting when a fluorescent or fluorescently labeled analyte flows past the detection region (see, e.g., ABI 3700 Sequencing systems, Agilent 2100 Bioanalyzer and ALP systems, etc.)

Still other detection systems direct a scanning laser at surface bound analytes to determine where, on the surface, the analytes have bound. Such systems are widely used in molecular array based systems, where the positional binding of a given fluorescently labeled molecule on an array indicates a characteristic of that molecule, e.g., complementarity or binding affinity to a given molecule (See, e.g., U.S. Pat. No. 5,578,832).

Notwithstanding the availability of a variety of different types of optical detection systems, the development of real-time, highly multiplexed, single molecule analyses has given rise to a need for detection systems that are capable of detecting large numbers of different events, at relatively high speed, and that are capable of deconvolving potentially complex, multi-wavelength signals. Further, such systems generally require enhanced sensitivity and as a result, increased signal-to-noise ratios with lower power requirements. The present invention meets these and a variety of other needs.

BRIEF SUMMARY OF THE INVENTION

The present invention is generally directed to systems and methods for monitoring a number of different optical signals from a number of sources of such signals and particularly a number of different and discrete sources of such signals. The methods and systems are particularly useful in monitoring chemical and biochemical reactions of interest from an array of reaction regions on a substrate where such reactions are taking place. Of particular interest are the use of these methods and systems in such analytical operations involving relatively high speed, low level signal generation as is found in single molecule analyses, e.g., in nucleic acid sequencing reactions.

In a first aspect, the invention provides an analytical device that comprises a substrate, and a plurality of signal sources disposed upon the substrate, the signal sources being arrayed upon the substrate in a plurality of substantially parallel rows, each of the plurality of parallel rows comprising a plurality of signal sources. Within or upon such substrate, two adjacent signal sources in a row are spaced apart by a first distance, and wherein two adjacent rows of signal sources are spaced apart by a second distance, wherein the second distance is at least three times greater than the first distance.

The invention also provides an analytical system. The system comprises a substrate having a plurality of discrete signal sources disposed thereon, an excitation light source, an optical train positioned to transmit excitation light from the excitation light source to the substrate to illuminate a first plurality of illuminated signal sources and a second plurality of illuminated signal sources, and image signals from the plurality of illuminated signal sources onto an array detector. In such context, one or more of the substrate and the optical train are configured such that the first and second plurality of illuminated signal sources is spaced from the other by a first distance of that is at least three times a cross sectional dimension of an image of a signal from a signal source imaged onto the array detector.

The present invention also provides a method of analyzing a plurality of signal sources. The methods typically comprise providing a substrate having a plurality of discrete signal sources disposed thereon. A first plurality of signal sources and a second plurality of signal sources are then illuminated, wherein the first plurality of illuminated signal sources are spaced apart from the second plurality of illuminated signal sources by a distance that is greater than three times a cross sectional dimension of an image of the signal source imaged on a detector array. The signal sources are then imaged on a detector array.

The invention also provides an analytical system, that comprises a substrate having a plurality of signal sources disposed thereon, an excitation light source, and an optical train configured to receive excitation light from the excitation light source, direct it onto the substrate in at least first and second substantially parallel linear illumination profiles, wherein the first and second linear illumination profiles are spaced apart on the substrate by a distance that is at least two times a width of the first linear illumination profile, and receive optical signals from the substrate an image the oiptical signals onto a detector array.

In an additional aspect, the invention provides an analytical system, comprising a substrate comprising a plurality of discrete signal sources disposed thereon, wherein at least a first subset of signal sources are positioned in a first substantial linear orientation, and a second subset of signal sources are positioned in a second substantially linear orientation that is substantially parallel to the first linear orientation. The system of this aspect of the invention also comprise a light source and an optical train for directing light from the light source to the substrate in at least first and second substantially parallel linear illumination profiles. The first linear profile illuminates the first subset of signal sources and the second illumination profile illuminates the second subset of signal sources.

Relatedly, the invention provides a method of detecting fluorescent signals from a plurality of signal sources on a substrate, comprising directing excitation radiation at portions of the substrate occupied the plurality of signal sources on a substrate while not directing excitation radiation at portions of the substrate not occupied by the signal sources.

In yet another aspect, the invention provides a system, that comprises a substrate comprising a plurality of discrete signal sources. The system also includes an excitation light source, and an optical train positioned to receive excitation light from the excitation light source and direct the excitation light to the substrate. The optical train is configured to direct excitation light in a substantially linear illumination profile at a plurality of signal sources, simultaneously, and simultaneously receive optical signals from the plurality of signal sources and direct the optical signals upon an imaging detector, to detect the optical signals from the plurality of signal sources.

The invention additionally provides a system, comprising a substrate having at least first and second rows of signal sources disposed thereon. Also included are an excitation light source, and an optical train, positioned to receive excitation light from the excitation light source and direct the excitation light to the substrate, wherein the optical train is configured to divide the excitation light into at least first and second discrete beams, and direct each of the at least first and second discrete beams in a substantially linear illumination profile at the substrate, wherein the first beam simultaneously illuminates a plurality of signal sources in the first row of signal sources, and the second beam simultaneously illuminates a plurality of signal sources in the second row of signal sources.

In a related aspect, also provided is a system, comprising an excitation light source, an optical train positioned to receive excitation light from the excitation light source and direct excitation light to the substrate. The optical train comprises a polarizing beam splitter to split the excitation light into at least first and second polar component beams, and optical components for directing each of the first and second polar component beams to different locations on the substrate.

In still another aspect, the invention provides a method of analyzing a plurality of signal sources on a substrate. The method comprises providing at least first and second adjacent signal sources on a substrate and selectively directing excitation radiation at the first and second signal sources while not substantially illuminating space between the first and second signal sources.

DETAILED DESCRIPTION OF THE INVENTION

I. Introduction

Figure 1:
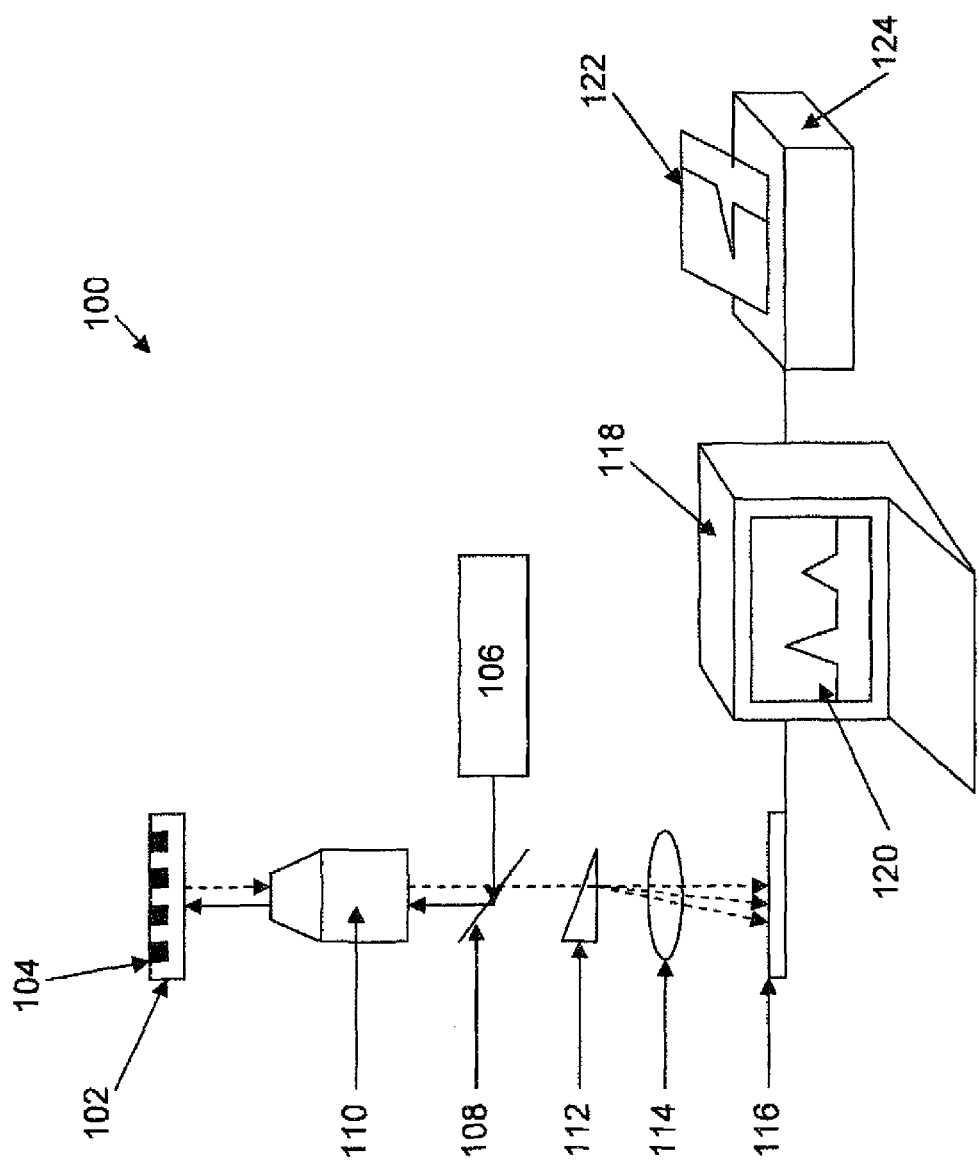
FIG. 1 is a schematic illustration of an overall system the present invention.

The present invention is generally directed to optical detection or monitoring systems, methods enabled by such systems, and components of such systems for concurrently illuminating multiple discrete points of interrogation or discrete optical signal sources, e.g., bearing fluorescent materials, on analytical substrates, and, as a result, concurrently monitoring, in real-time, optical signals that emanate from multiple discrete sources of those optical signals. In particular, the optical detection and monitoring systems of the invention are generally capable of illuminating and/or monitoring discrete signals from potentially very large numbers of different signal sources, optionally separating and/or deconvolving such signals into constituent signal events, and doing so in real-time, despite that such signals may be changing rapidly, over time.

In accordance with preferred aspects of the invention, the systems and methods of the invention provide enhanced optical signal-to-noise ratios, and are capable of utilizing substantially lower illumination power, than systems that would employ a less selective illumination profile. This is generally accomplished by directing the illumination substantially at the regions of interest on an analytical substrate, while avoiding directing any illumination at regions of the substrate other than the regions of interest. By providing illumination substantially only where desired, one can reduce the illumination power directed at the substrate as a whole, and also substantially decrease optical signal noise sources, such as reflected illumination or "laser bleed through", autofluorescence, scattering, and the like. As a result of the reduction of such noise sources, the optical signal-to-noise ratio is increased dramatically and the detection fidelity is improved.

The systems of the invention thus include all or a portion of a collection of different functional elements. These elements include the multiple discrete sources that include the capability of generating optical signals. In preferred aspects, such sources include chemical, biochemical and/or biological reactants, or mimics of such reactants that are capable of generating optical signals that are indicative of their presence, reaction or conversion. While the sources may be capable of generating optical signals on their own, in preferred cases, a source of excitation radiation is also provided to excite optical signals, e.g., fluorescence, within the sources.

The systems of the invention also typically include optical elements that direct, separate, and/or otherwise alter optical signals from these sources (as well as excitation radiation directed at such sources), in order to ultimately derive optimal amounts of information from such signals when they are ultimately detected. Consequently, the systems of the invention typically include an optical detection system for detecting the potentially large numbers of signals that were directed from the sources, and optionally separated and/or otherwise altered by the optical elements.

Signals detected by the optical detection system are then recorded and processed by appropriate processing systems and data management processes to provide output of the system in user ready formats.

As alluded to previously, the systems of the invention are preferably applied in the monitoring of arrays or collections of spatially discrete chemical, biochemical and/or biological reactions that generate optically detectable signals, such as chromogenic reactions, luminescent or luminogenic reactions, or fluorescent or fluorogenic reactions. A few examples of preferred reactions include those that are regularly performed in the pharmaceutical, biotechnology and healthcare diagnostic fields, i.e., immunoassays, enzymatic assays, receptor assays, nucleic acid hybridization assays, nucleic acid synthesis reactions, cellular assays, and many others.

Typically, the progress of the reactions used in application of the systems described herein result in one or more of the consumption, production and/or conversion of a material, that is capable of generating an optically detectable signal, either alone, or in response to an external stimulus, e.g., excitation radiation. By way of example, certain reactants may become fluorescent upon reaction with another reactant, or may have their fluorescence altered or reduced upon such reaction. As such, the fluorescence emitted from the reaction in response to an excitation radiation will change as the reaction progresses. The systems of the invention provide for the source of such signals, e.g., the area in which the reaction occurs, including optionally, the reactants and/or products, the optical elements for collecting, directing and optionally separating and/or altering such signals from such sources, and the ultimate detection of such signals, as well as the manipulation of the resulting data to yield optimal value and information for the user.

The systems of the invention typically include all or a subset of a substrate that includes all or a subset of the sources of optical signals, an optional excitation light source, an optical train that includes the various optical elements for collection, direction and/or manipulation of the optical signals and optional excitation light, optical detectors for receiving, detecting and recording (or putting into a form for recordation) the optical signals, as well as processors for processing data derived from the optical detectors.

A general schematic representation of the system as set forth above, is illustrated in FIG. 1. As shown, the system 100 includes a substrate 102 that includes a plurality of discrete sources of optical signals, e.g., reaction wells or optical confinements 104. An excitation light source, e.g., laser 106, is optionally provided in the system and is positioned to direct excitation radiation at the various signal sources. This is typically done by directing excitation radiation at or through appropriate optical components, e.g., dichroic 108 and objective lens 110, that direct the excitation radiation at the substrate 102, and particularly the signal sources 104. Emitted signals from source 104 are then collected by the optical components, e.g., objective 110, and passed through additional optical elements, e.g., dichroic 108, prism 112 and lens 114, until they are directed to and impinge upon an optical detection system, e.g., detector array 116. The signals are then detected by detector array 116, and the data from that detection is transmitted to an appropriate data processing unit, e.g., computer 118, where the data is subjected to interpretation, analysis, and ultimately presented in a user ready format, e.g., on display 120, or printout 122, from printer 124.

The various functions, applications and components of the systems of the invention are set forth in greater detail below.

II. Substrate

A. Substrate

As alluded to previously, the substrates of the invention, as a general matter, provide the multiple discrete sources of optical signals. In the case of systems for monitoring reactions, such signal sources typically comprise discrete regions in which reactions are taking place and from which discrete optical signals may emanate. In a broad sense, such different regions may comprise reaction depressions, wells, or zones that are maintained discrete from other regions by any of a number of different mechanisms, including chemical or physical confinements. Merely by way of example, such regions may comprise discrete patches or zones of immobilized molecules on a surface of the substrate, such as in nucleic acid, protein, antibody or other immuno-arrays, where the reaction being monitored is the association of analytes with such immobilized molecules, they may include channels within a substrate, e.g., microfluidic channel regions, aggregations of capillaries or multiple regions within individual capillaries, or the like.

Alternatively or additionally, such regions may include structural confinements that maintain the reaction components within the discrete regions. Such structural confinements may include wells, depressions, channels, or other structures that retain reaction constituents. Such confinements may also include other barriers that effectively provide structural confinement through, e.g., the use of chemical barriers, e.g., hydrophobic regions surrounding hydrophilic regions on the substrate surface to retain aqueous reaction constituents within the hydrophilic regions.

In still other aspects, such regions may include combinations of the above, e.g., including immobilized reactants within structural confinements. In addition to structural confinements, the reaction regions may comprise optical confinements that may function as or in addition to structural confinements on the substrates, that serve to minimize observation volumes on the substrate through the confinement of excitation illumination and/or the collection of emitted optical signals from relatively small areas or volumes at the reaction region. Such optical confinements may include, e.g., waveguides, such as zero mode waveguides, optical gratings, optical coatings or the like, that can yield the excitation or observation volumes desired on the reaction regions on the substrates.

Typically, the substrates will comprise an optically transparent layer upon which are disposed the reaction regions that provide the discrete sources of optical signals. The optically transparent layer may generally comprise any of a number of transparent solid materials, depending upon other components of the substrate. Such materials include inorganic materials, such as glass, quartz, fused silica, and the like. Alternatively, such materials may include organic materials, such as polymeric substrates such as polystyrene, polypropylene, polyethylene, polymethylmethacrylate (PMMA), and the like, where PMMA is particularly useful in fluorescent or fluorogenic reactions, as it has relatively low auto-fluorescence.

In preferred aspects, the substrates include zero mode waveguides as the optical confinements to define the discrete reaction regions on the substrate. Zero mode waveguides have been described in, e.g., U.S. Pat. No. 6,917,726, the full disclosure of which is incorporated herein by reference in its entirety for all purposes. Briefly, such waveguides comprise a core disposed through a cladding layer, which in the case of applications to reactions, comprises an aperture disposed through the cladding layer that can receive the reactants to be monitored. Typically, the aperture has at least one cross-sectional dimension, e.g., diameter, which is sufficiently small that light entering the waveguide is prevented in some measure from propagating through the core, effectively resulting in a very small portion of the core and its contents being illuminated, and/or emitting optical signals that exit the core. In the case of optical signals (and excitation radiation), the waveguide cores will typically be between 1 nm and 200 nm, and are preferably between about 10 and 100 nm, and more preferably between about 30 and about 100 nm in diameter.

Optical confinements are typically provided upon the substrate in an array format where a plurality of confinements is provided upon the substrate. In accordance with the invention, arrays of confinements, e.g., zero mode waveguides, are provided in arrays of more than 100, more than 1000, more than 10,000, or even more than 100,000 separate waveguides on a single substrate. In addition, the waveguide arrays typically comprise a relatively high density of waveguides on the surface of the substrate. Such high density typically includes waveguides present at a density of greater than 10 zero mode waveguides per mm$^2$, preferably, greater than 100 waveguides per mm$^2$ of substrate surface area, and more preferably, greater than 500 or even 1000 waveguides per mm$^2$ and in many cases up to or greater than 100,000 waveguides per mm$^2$. Although in many cases, the waveguides in the array are spaced in a regular pattern, e.g., in 2, 5, 10, 25, 50, 100, 1000 or more rows and/or columns (with each row or column having 2, 5, 10, 25, 50, 100, 1000 or more waveguides) of regularly spaced waveguides in a given array, in certain preferred cases, there are advantages to providing the organization of waveguides in an array deviating from a standard row and/or column format. For example, in certain preferred aspects, the signal sources on the substrate are arrayed in a plurality of substantially parallel lines where sources in a given line are substantially regularly spaced at a first distance, but where adjacent parallel lines of sources are spaced at a second distance that is greater than the first distance. As used herein, the term substantially parallel means that a line that defines or touches the positioning a plurality of signal sources in a first row is within 10° of parallel, preferably within 5° and more preferably within 1° of parallel, of a line defining or touching a plurality of signal sources in a second row.

Figure 2:
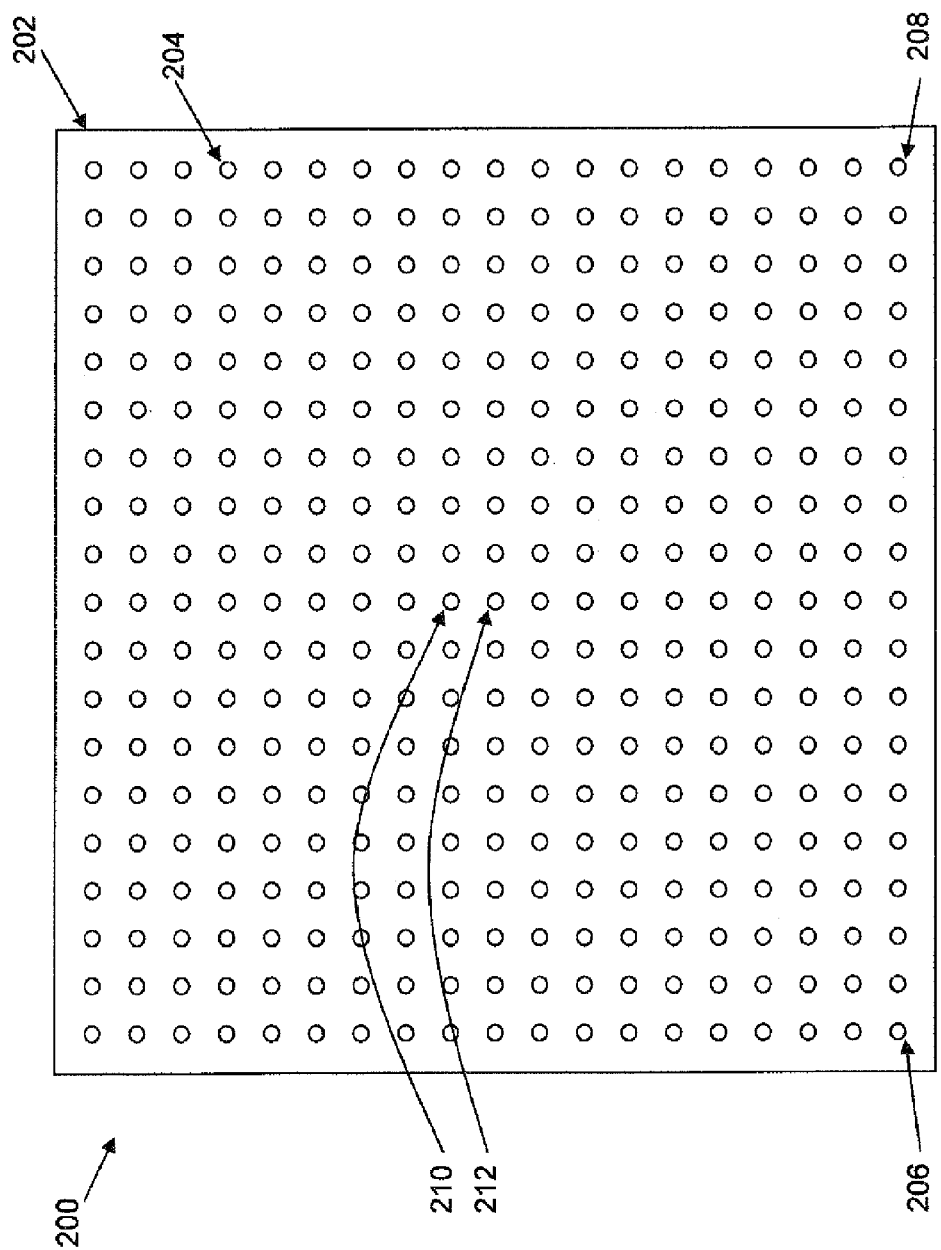
FIG. 2 provides a schematic illustration of an array of signal sources on a substrate, such as zero mode waveguides.

FIGS. 2 and 3 show alternative arrangements of optical signal sources arrayed on a substrate. FIG. 2 shows an array 200 of sources of optical signals (shown as an array of zero mode waveguides 204 in a substrate 202) that includes regularly spaced and consistently sized sources of optical signals. As noted previously, the signal sources may also be spaced to account for optical manipulations of the signals emanating therefrom. For example, as discussed in greater detail below, in some cases, optical signals are spatially separated into component elements, e.g., light of different wavelength ranges, indicative of different signaling elements, i.e., fluorescent reagents having differing emission spectra. In such cases, it may be desirable to provide sufficient spacing between adjacent signal sources on the substrate to prevent overlap of the spatially separated signals derived from those sources, when those separated signals are incident upon the detector, as set forth below. In this case, increased spacing may only be required in one dimension, e.g., providing sufficient spacing between rows of signal sources, but not necessarily between the columns of signal sources in the array. Alternatively, such additional spacing may be provided in two dimensions. In the case of arrays of signal sources where the signals are subjected to spatial separation before detection, such spacing between adjacent signal sources may generally range from about 0.1 µm to about 10 µm or more, and is preferably from about 0.8 µm to about 3 µm or more.

Figure 3A:
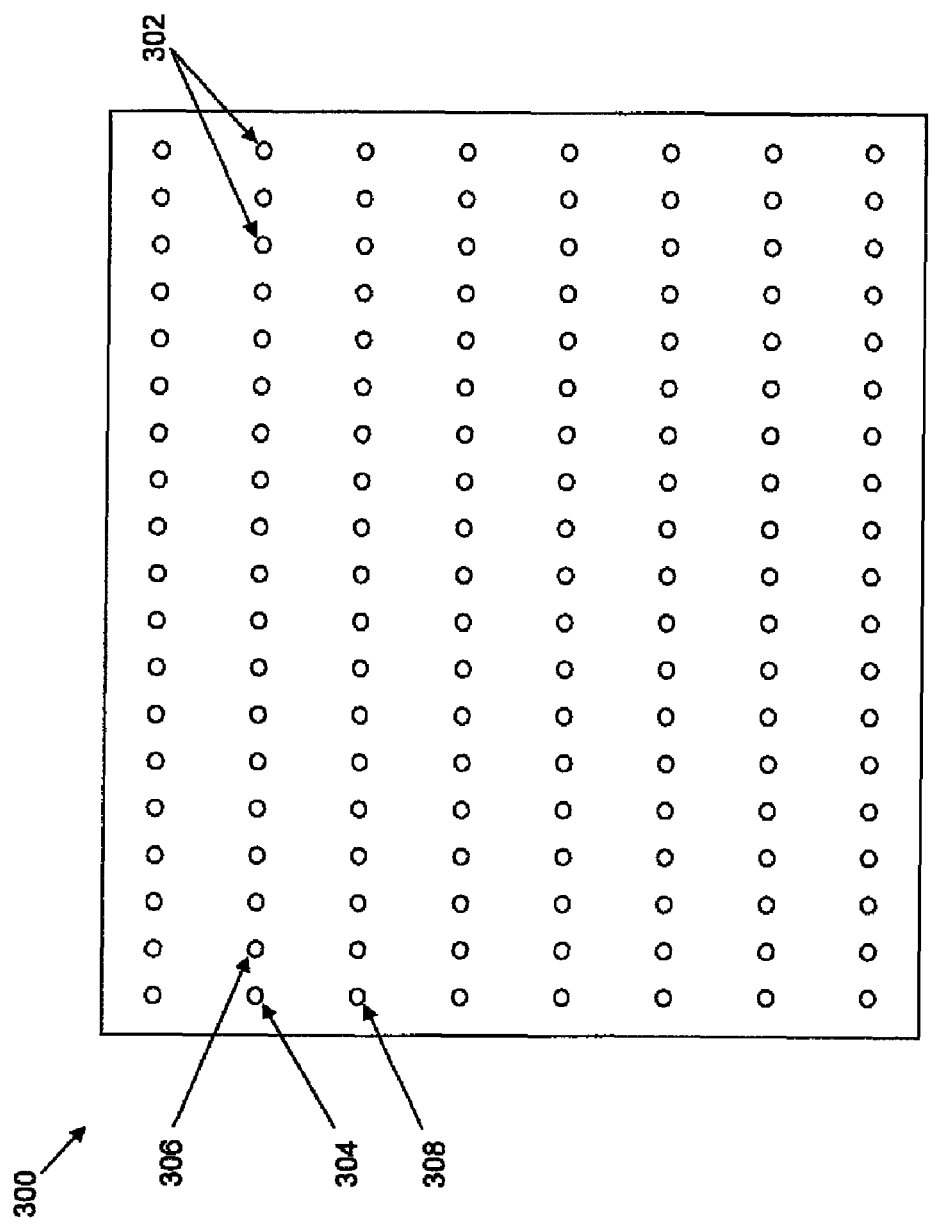
FIGS. 3A and 3B illustrate alternative configurations of signal sources to accommodate signal detection systems off the invention.

Accordingly, as shown in FIG. 3A, an array 300 of sources 302 is provided where the spacing between adjacent sources is maintained relatively small in one dimension and relatively larger in the other dimension. Typically, this results in arrays of sources that are arranged in parallel rows or columns where the intra-row spacing is less than the inter-row spacing. Thus, the distance between source 304 and 306 is less than the spacing between sources 304 and 308. By providing greater spacing in one dimension allows for spectral separation of signal components focused onto a detector array in that same dimension, without overlap of the imaged signals from other adjacent signal sources. Typically, because signal component separation is typically carried out in one dimension, e.g., the inter row dimension, the spacing between adjacent rows of signal sources such as ZMWs will be sufficient that when the separately resolved signal components from each ZMW are imaged onto the detector array, there is no overlap between signals from adjacent rows. Thus, if one assumes that a ZMW is imaged upon an array, and one wishes to include, two, three, or preferably four or more image components on the array, the spacing between the rows will correspond to at least 1×, 2× or 3× or more of the space required to resolve an individual component, which is roughly equivalent to size of an imaged signal component. This allows for sufficient inter row spacing to image 2, 3, 4 or more signal components without signal overlap. In its simplest form, this means that the spacing between rows will typically be at least 2×, 3× or 4× or more of the spacing between signal sources that are in the same row. Alternatively, the spacing between adjacent signal sources in different rows may be based upon the size of the illumination spot, or in the case of linear illumination, the width of the illumination line. In particular, in order to assure sufficient spacing between illuminated signal sources, the spacing between adjacent rows of signal sources may be 2× the width of the illumination spot or line, or even 3× the width of the illumination spot or line, 4× the width of the illumination spot or line, or even greater. In certain aspects, the pitch of signal sources within a given row, e.g., as measured center to center, can range from about 100 nm to about 1 mm, while in preferred aspects, it will range from about 100 nm to about 1 µm or even from about 200 nm to about 500 nm. In contrast the pitch between adjacent rows will typically be from about 2× to about 10× that of the intra-row pitch, and typically at least 3×. As such, the inter row pitch for signal sources will typically range from about 200 nm to about 10 mm, with certain preferred substrates having an inter-row pitch of from about 200 nm to about 1500 nm to about 3 µm. As will be appreciated the pitches (intra- and inter-row) may fall anywhere within the ranges in preferred aspects and may also fall outside of these ranges in many cases.

Figure 4:
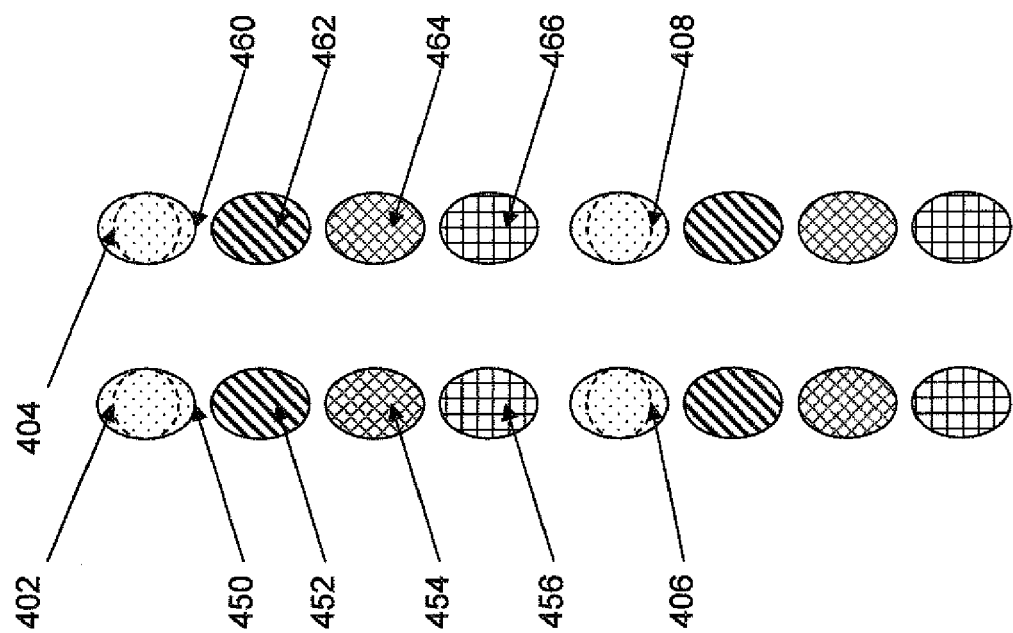
FIG. 4 schematically illustrates the separated imaged signals derived from the substrate shown in FIG. 3A, providing an overlay of the signal sources from that substrate on the imaged signals.

The benefit of this aspect of the invention is schematically illustrated in FIG. 4. As shown, the spacing of a signal source array is overlaid upon a schematic of a spectrally resolved image of the signals emanating from those signal sources. In particular, each signal source 402 gives rise to the image of a plurality of signal components (typically of different wavelength ranges) that are spatially separated and imaged upon different regions of a detector array (as images 450-456). By providing sufficient spacing between signal source 402 and 406, and 404 and 408, one provides image space upon the detector array top accommodate the full range of the imaged signal components from each signal source, e.g., images 450-456 and 460-466.

The foregoing aspects of the invention are particularly useful in the resolution of multiple spectrally differing signal components from a single signal source. For example, in the case of fluorescent compounds that are used in monitoring reactions, the foregoing aspects of the invention are useful in permitting resolution of signals from mixtures of fluorescent compounds that provide at least 2, 3, 4 or more different fluorescent emission spectra in response to a particular excitation radiation. For example, one can optically resolve and thus differentiate at least 2, 3, 4 or more spectrally differing fluorescent emission profiles from a single signal source. As will be appreciated, such systems are also useful in resolving other spectrally differing signal components whether fluorescence based or otherwise, e.g., luminescent, colorimetric, and the like.

Figure 3B:
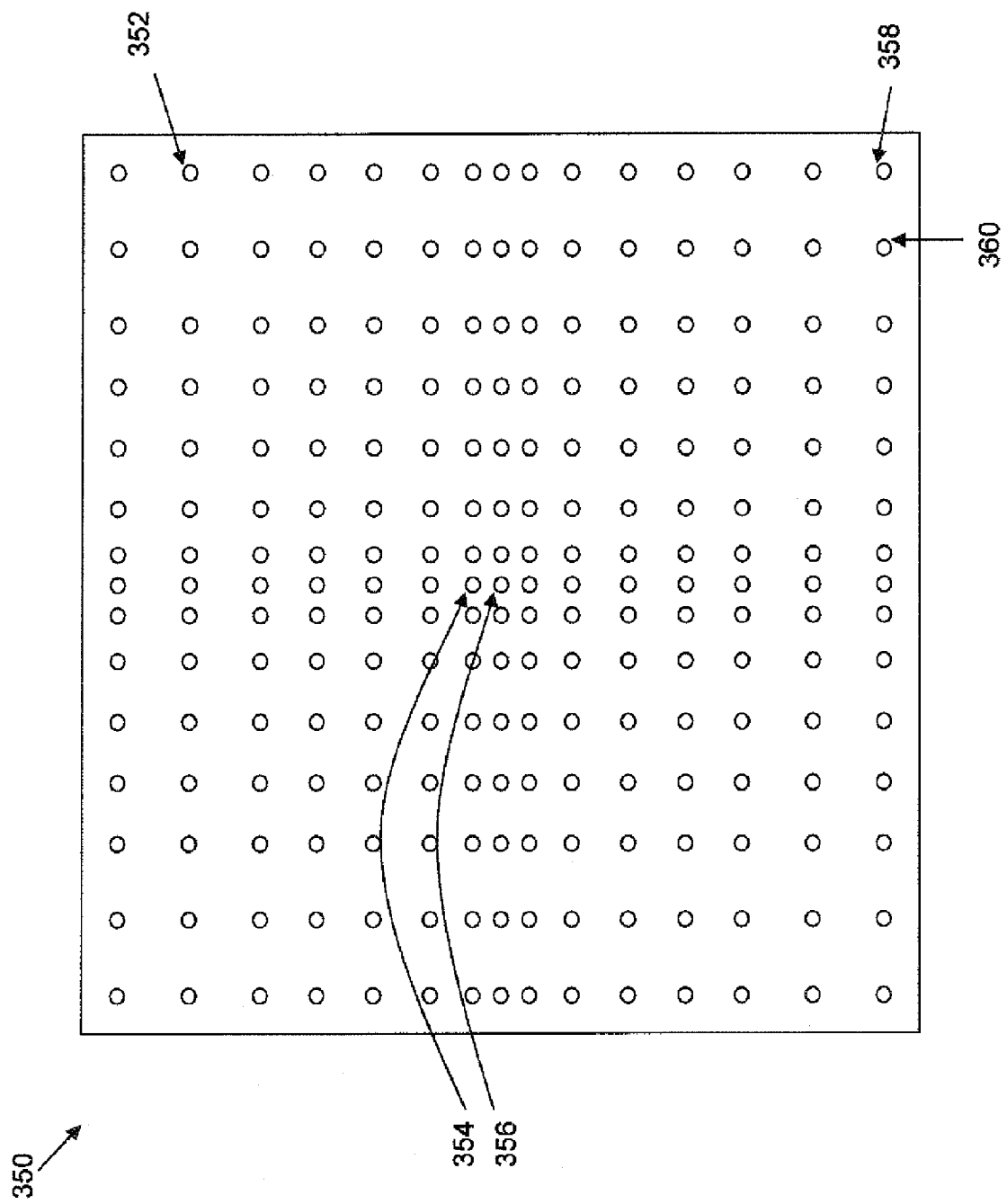

Additionally or alternatively, source spacing may be arranged to accommodate optical aberrations in the overall optical system, or to accomplish other objectives. This aspect of the invention is schematically illustrated in FIG. 3B. As noted previously, in some cases the sources at the periphery of the array, e.g., sources 206 and 208 in FIG. 2 may be less well resolved, optically, than, e.g., sources 210 and 212. In some cases, it may be the case that aberrations could be sufficient to prevent resolution of the peripheral sources, e.g., 206 and 208. Accordingly, as shown in FIG. 3B, an array 350 of sources 352 is provided where the spacing between adjacent sources is increased as a function of the distance from the center of the object image. For example, as shown, signal sources that are nearer the center of the object field represented by the array 350, e.g., sources 354 and 356 are closer together in at least one dimension, than are sources that further away from the center of the object field, e.g., sources 358 and 360, which are more widely spaced in at least one dimension than the more central signal sources. Thus, the space, in at least one dimension between two sources at a first distance from the center of the object field of the optical system will be less than the space, again in at least one dimension, between two sources that are at a second, greater distance from the center of the object field. The spacing between adjacent signal sources may be varied in only one dimension, e.g., varied from left to right, but not from top to bottom, or it may be varied in both dimensions. In the case where the spacing is varied in both dimensions, it will be appreciated that the distance between any two signal sources at the center of the object field, e.g., is less than the space between any two signal sources further away from the center, i.e., on the periphery, of the object field. The foregoing permits greater effective multiplex analysis of arrays of signal sources, such as ZMWs.

Additional arrangements of array elements can be specifically tailored to fit a particular aberration of particular optical systems. For example, if a dominant optical aberration forms a resulting image spot size or shape that is dependant upon field location, then that size or shape can be accommodated in the design of the array of sources by, e.g., appropriately spacing the sources to avoid overlap in image of adjacent sources, or the like. Similarly, if the shape of an imaged source is distorted in one dimension so as to potentially overlap with images of neighboring sources, that source can be dimensioned to reduce that dimension and avoid the overlap, e.g., providing elliptical or rectangular sources.

The foregoing permits greater effective multiplex analysis of arrays of signal sources, such as ZMWs.

B. Substrate Interface

The substrates of the invention are typically interfaced with the overall system through an appropriate mounting stage that secures the substrate, provides translational capability to the substrate, e.g., relative to the optical system, and optionally provides additional functionalities, e.g., fluidic interfaces, thermal regulation, e.g., heating or cooling, positional registration, and the like. The mounting stage will also typically include a positioning element that ensures proper positioning and/or orientation of a substrate upon the stage, for subsequent analysis. Such positioning systems may include keyed structures on the substrate that are complementary to a corresponding structure on the mounting stage. These may include simple structures, e.g., tooth/notch structures, truncated corner structures, or other distinctive and complementary structures. Alternatively, the keying elements may include electronic keys, such as metal contacts and associated electronic components on the substrate and mounting stage, that indicate when a substrate is positioned properly and in the correct orientation for subsequent analysis. Such key elements may be provided encoded for each substrate, e.g., through incorporated memory elements on the substrate, or through the position and orientation of electrical contacts, to indicate a specific substrate, e.g., lot number, etc. Such identification systems may provide an ability to ascertain whether a given substrate has been used previously, and to what effect. Typically, the mounting stage includes a well or recessed component configured to receive the substrate or the packaged structure containing the substrate, e.g., a multiwell plate format, as well as a biasing mechanism, e.g., spring, clip or other mechanism, for forcibly retaining the substrate in a fixed position on the stage. A variety of different mounting stages, keying elements, and translation systems may be employed in the context of the present invention. For example, mounting stages may range from simple platforms with clip based biasing components to retain the substrates in position, to more complex mounting stages, e.g., that may include slots configured for the substrates to be inserted therein and maintained in position relative to the other components of the system, e.g., akin to a tape receiving mechanism for a video or cassette tape system. Such systems may include enclosures around the mounting stage, in order to provide for controlled environments surrounding the substrates when in use. Typically, the mounting stages will include keying elements that ensure that the substrate is appropriately oriented upon the mounting stage, and may include interface components for identification of the substrate or the application for which the substrate is intended, e.g., through a bar code reader on the mounting stage and a bar code applied to the substrate, or through an electronic encoding element, e.g., an RFD element.

Figure 14:
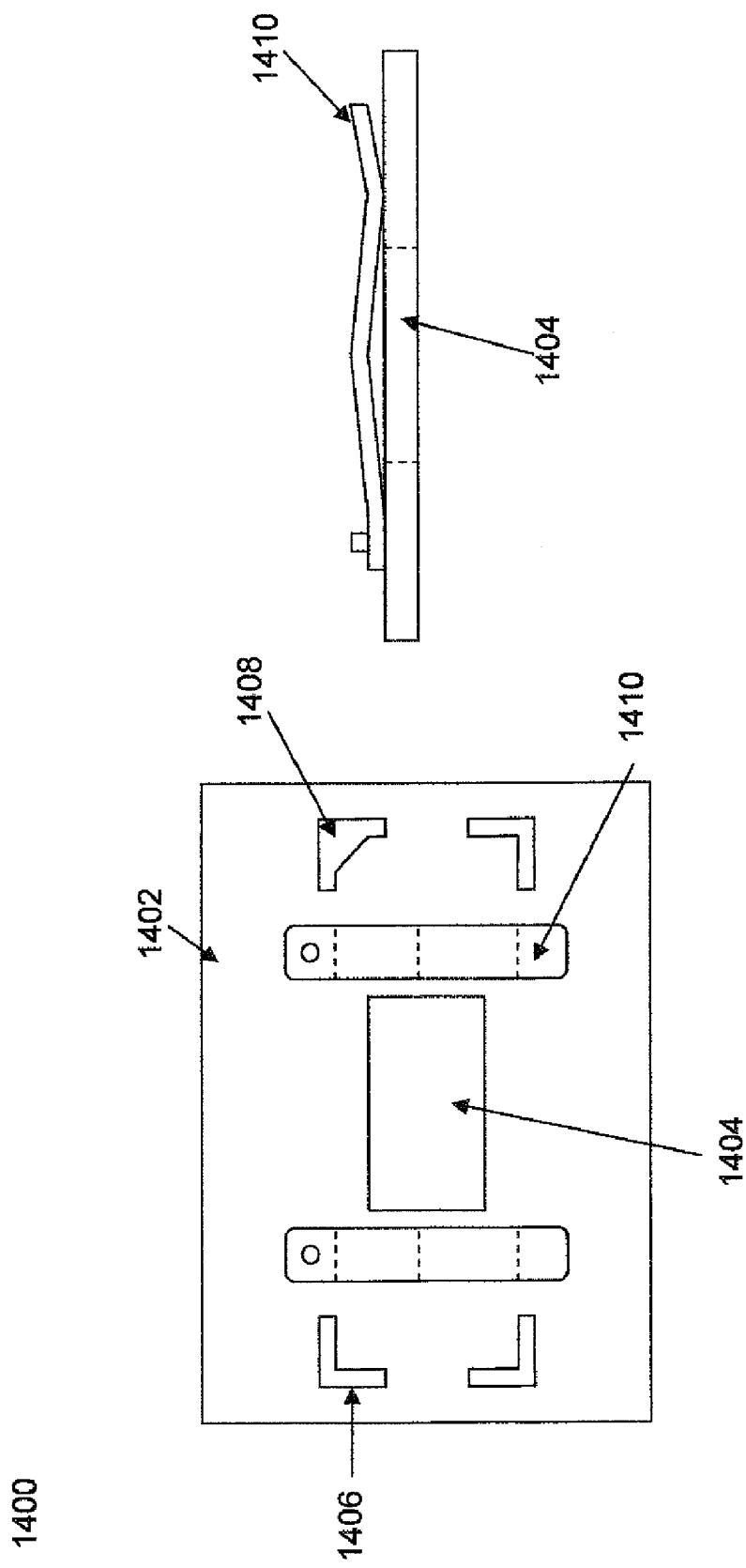
FIG. 14 provides a schematic illustration of an example of a mounting stage useful in conjunction with the substrates and systems of the invention.

One example of a relatively simple mounting stage is shown in FIG. 14. As shown, the mounting stage 1400 includes a platform 1402 having a mounting region 1404 that receives the substrate (not shown). The mounting region is typically disposed over an aperture 1406 in the platform 1402 that allows observation of the substrate from underneath. Also as shown, the mounting stage includes structures that facilitate the positioning and alignment of the substrate on the platform. These may include, e.g., ridges 1406, recesses or wells, for positioning the substrate, and alignment structures 1408, such as pins, bevel structures, tabs, or the like, that correspond to a complementary structure on the substrate, e.g., holes or notches. As noted above, securing mechanisms may also be provided for locking the substrate in place, such as biasing mechanism 1410, shown as a clip or a closable cover element, shown also from a side view. Additional components may be provided on the mounting stage, such as a heating or cooling element, additional optical components, and other interfacing elements.

Figure 15:
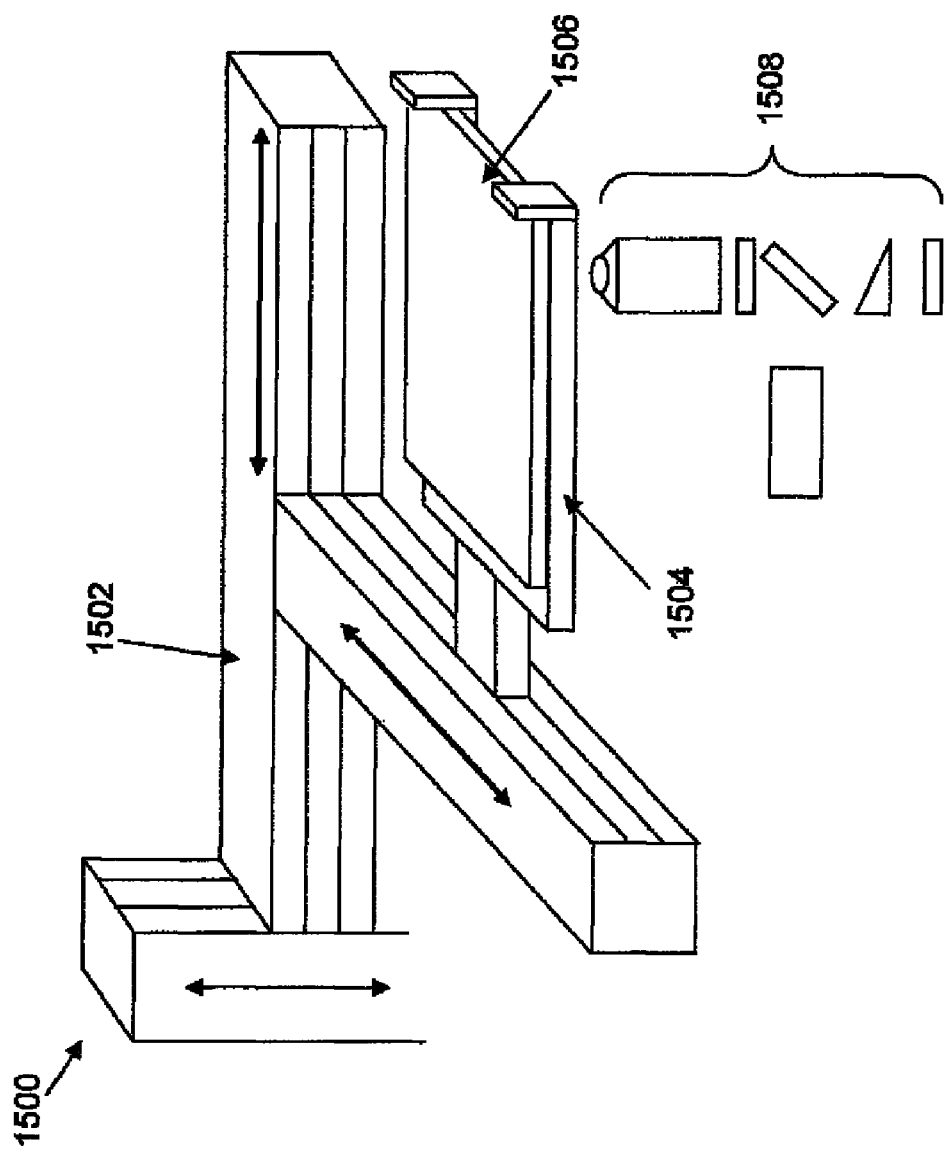
FIG. 15 schematically illustrates a robotic system for use in conjunction with the invention.

The mounting stage is also typically coupled to a translation system for moving the stage in two or three dimensions relative to the optical system. The translation system allows scanning of the entire array of signal sources on a substrate, as well as providing an ability to move the substrate toward or away from the optical system for, e.g., focusing, removal of the substrate, addition of components to the substrate, or the like. A variety of x-y-z translation systems are readily available. Additionally, robotic systems are readily available for automating the translation functions of the mounting stage in accordance with preprogrammed instructions. FIG. 15 shows a schematic representation of an entire system 1500 including a schematically represented translation system 502 coupled to a mounting stage 1504, supporting substrate 1506 over optical train 1508. As shown, the robotic system includes the capability to move the substrate in any of the x, y, or z dimensions.

Robotic systems may also include components that position substrates upon the mounting stage, apply reagents to the substrates, and the like. A wide variety of such robotic systems that may be applied to the present invention are generally commercially available from, e.g., Tecan, Inc., Caliper Life Sciences, Inc., Beckman, Inc., and the like.

Robotic systems may also include components that position substrates upon the mounting stage, apply reagents to the substrates, and the like. A wide variety of such robotic systems that may be applied to the present invention are generally commercially available from, e.g., Tecan, Inc., Caliper Life Sciences, Inc., Beckman, Inc., and the like.

III. Excitation Source

As noted previously, in preferred applications, the systems of the invention are used to monitor luminescent or fluorescent signals emanating form the plurality of discrete signal sources. As such, in many cases, the systems of the invention include a source of excitation radiation. Excitation light sources will generally depend upon the nature of excitation radiation needed for a particular application, e.g., as dictated by the reagents and configuration of a given analysis. For example, the light source may include lamps, e.g., halogen, Mercury, Xenon, or the like, LEDs, lasers, laser diodes, or any other light source capable of directing electromagnetic radiation of a desired excitation wavelength or wavelength range, to the signal sources on the substrate. In preferred aspects, lasers are preferred as the excitation radiation source, due to the narrow bandwidth and intensity of radiation that they generate in desired excitation wavelength ranges. A variety of different laser types are generally useful for these applications, and include, e.g., ion lasers, solid state direct diode lasers, diode-pumped solid state lasers (DPSS), solid state frequency converted crystal lasers, and the like. In some cases multiple sources may be employed in order to provide multiple different excitation wavelengths. By way of example, in cases where the signal sources include fluorescent compounds, e.g., compounds labeled with fluorescent dyes, multiple different excitation sources may be provided for the various different excitation spectra for such compounds. For example, in the case of compounds labeled with Alexa648 dyes, it will typically be desirable to provide at least an excitation source that provides excitation radiation range that includes light at 648 nm (the respective excitation wavelengths for these dyes). Alternatively, if not provided at the nominal peak of the dye absorption curve, the lasers will include sufficient absorbtion efficiency for the dyes used, such as for Alexa 546, where the peak absorption efficiency is closer to 561 nm. In the cases of multiple different dyes, different lasers, e.g., having different wavelength ranges may be used.

IV. Optical Train

As noted previously, the overall systems of the invention typically include an optical train for the direction of excitation radiation to the substrate and the plurality of signal sources thereon, and/or for directing emitted signals from these sources to a detection system that quantifies and records the signal from each signal source. The optical trains used in the overall systems described herein typically include a number of different optical components for use in focusing, directing, splitting, separating, polarizing, and/or collimating the excitation radiation and/or the signals emanating from the discrete sources of signals.

Figure 5:
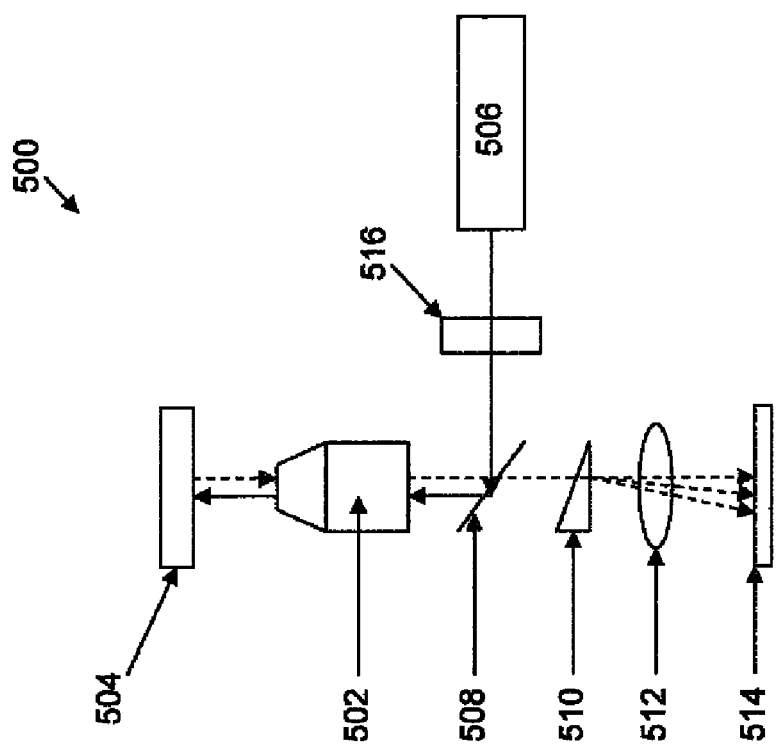
FIG. 5 schematically illustrates the substrate and optical train of the systems of the invention that includes optical componentry for the separation and detection of spectrally resolvable signal components.

A schematic illustration of one optical train is shown in FIG. 5. As shown, the optical train includes an objective lens 502 that is proximal to the substrate 504, and which focuses excitation radiation, e.g., from laser 506, upon a desired location of the substrate, and collects emitted optical signals from the substrate. The optical train will also typically include one or more dichroic mirrors/filters 508, that selectively reflect or pass excitation light and emitted optical signals, to effectively separate signal radiation from reflected or otherwise errant excitation radiation.

The optical train may also optionally include signal separation optics, e.g., to separate optical signals of different wavelengths or direct them to different locations on a detection system. For example, the optical train may include prism 510 that receives the optical signs as from the signal sources, that may include signals of several different primary wavelengths. Alternatively, sets of dichroic filters may be used in a cascading arrangement, to selectively direct each different spectral signal component to a different detector or detector region.

In the case of a prism as a separation element, upon passing through the prism 510, the different wavelength signals are diffracted to different degrees, and as a result, are directed, optionally through additional optical components, i.e., imaging lens 512, at different angles toward the detection system, e.g., detector array 514 allowing for their separate detection and quantitation.

The ability to separate such signals is of particular value in monitoring signal sources that include multiple different reagents that each have a different fluorescent emission spectrum, indicative of a different specific reagent, reaction and/or interaction. A variety of other optical components may be employed in spectrally separating the optical signals, including cutoff filter sets, dichroics, optical gratings, and the like.

Such components will typically be arranged to direct different portions of each optical signal to different detectors or, preferably, different locations upon the same detector or array of detectors. In accordance with the invention, different signals may be spectrally resolved by differentially imaging such signal components onto the detector, e.g., detector array 514. Such differential imaging may be spatially different, e.g., by being directed to different detectors or locations on the same detector, or they may conformationally different, e.g., providing an imaged signal that is of a different shape than an image of a different signal component, such that it can be resolved.

Other components that separate portions of the optical signals are also optionally included in the optical train, depending upon the application to which the system is to be put, including spatial filters, e.g., to confine the optical signals that are directed to the detector, polarizing filters, to pass signals that are in one polar optical plane, or the like. For example, in addition to separation of signals of differing wavelengths, the optical train may also include splitters, e.g., beam splitters, optical gratings, lens or microlens arrays, and the like, that serve to divide up the excitation radiation and/or the emitted signals to direct it to different locations, or other optical components that change the spatial configuration of excitation radiation, e.g., optional optical grating 516. In some cases, additional filters may be added after the laser to filter the main laser line by removing or reducing any optical noise that may be inherent in the laser, as well as in front of the detectors to reduce or remove any unwanted stray light that may be generated or reflected from the system as a whole, or the ambient light.

In particular, in certain aspects, one or more of the optical train and/or the excitation radiation source may be configured so as to provide excitation illumination of a large number of discrete signal sources on the substrate simultaneously, while optionally preventing or reducing illumination of spaces on the substrate outside of the signal sources. In particular, non-relevant illumination, e.g., illumination directed at portions of the substrates that do not include signal sources, can give rise to substantial amounts of optical noise that will reduce the optical signal-to-noise ratio of the system, thus driving down the sensitivity of the system. In particular, light scatter from excess radiation, reflected laser illumination that passes through the optical train ("laser bleed through"), and autofluorescence of the substrate materials are a large component of optical noise in fluorescence systems. Disadvantages of excess illumination also flow through the system, including providing increased power requirements for the excitation light source to ensure a diffuse illumination pattern provides sufficient illumination power in all desired locations. This leads to increased cost and power dissipation requirements due to the incorporation of lasers with higher powers. Additionally, excessive illumination can impact data processing parameters by providing irrelevant data in spaces between relevant signals. Further, thermal effects, e.g., heating, are a function of the amount of laser power directed at chemical and biological samples, and can substantially negatively impact applications of these systems.

In the context of arrays of zero mode waveguides, for example, the optical train and/or the excitation radiation source provide illumination to a large number of zero mode waveguides, simultaneously. As noted below, the optical trains are also typically capable of collecting and detecting signals from the same or similar large numbers of the signal sources, or in this example, zero mode waveguides. The systems typically illuminate at least 2 signal sources simultaneously, preferably, greater than 10 signal sources simultaneously, and more preferably, greater than 100 signal sources, simultaneously. In some cases, it may be desirable to use the systems described herein, for the excitation of 1000, 10,000 or more discrete signal sources. Systems that split excitation beams or apply multiple excitation sources (both with, or without, beam splitting) are particularly useful for directing excitation radiation to larger numbers of signal sources.

Simultaneous illumination with excitation radiation over large numbers of signal sources may generally be accomplished through a variety of different means, as noted above. For example, one may focus a relatively large spot size upon a large array of signal sources. However, as will be appreciated, because laser power is limited, and indiscriminate illumination may cause certain adverse effects, e.g., heating, autofluorescence, and consequently reduced optical signal: noise ratios (SNR), it may be desirable to avoid illuminating non-signal generating portions of the substrate. For example, in the case of arrays of zero mode waveguides using a thin film metal cladding layer, spaces between signal generating regions are highly reflective. Such reflected activation radiation gives rise to elevated noise levels for the system. In addition, the substrate materials may also autofluoresce in response to illumination, giving rise to additional sources of optical noise to the system. As such reducing noise contributions from irrelevant portions of a substrate is desirable.

In some cases, larger excitation regions may be provided by directing multiple different excitation sources at a given substrate to provide illumination of larger numbers of signal sources, e.g., laser 506 and optional additional lasers (not shown). Unfortunately, use of multiple different sources may provide issues regarding differences between the individual sources, e.g., wavelength, frequency or intensity of illumination that may impact the signals resulting therefrom, e.g., rendering slightly different signal profiles. Additionally, such multiple excitation source systems may still give rise to the problems of excessive illumination of the substrate, as a whole. Similarly, excitation light beams may be divided into multiple beams, e.g., using beam splitters, optical gratings or other optical components, as described elsewhere herein, to direct multiple discrete excitation illumination spots at different locations of the substrate, and as a result, illuminating larger numbers of signal sources thereon. In a related aspect, lenses may be provided that stretch the beam spot into an elliptical or elongated spot or line shape.

In certain preferred arrangements, individual or multiple excitation radiation source(s) may be manipulated to provide preferential illumination on the signal sources on a substrate, and reduce or eliminate illumination at regions of the substrate not occupied by the signal source(s). A number of methods may be used to modulate the illumination profile of the excitation light source to preferentially provide excitation illumination at the signal sources on the substrate, and, in particularly preferred aspects, less illumination at the spaces not occupied by such signal sources. In general, this is accomplished by using optical elements that provide an illumination profile at the object plane of the optical train, e.g., the substrate, that peaks in intensity at positions in the object plane that correspond, at least in part, to the position of the signal sources on the substrate. A variety of different optical elements may be used to achieve this illumination profile. For example, where illumination at a low frequency is not an issue for analysis of the signal sources, one may simply employ reciprocating beam, e.g., through the use of a galvo-equipped laser system. In cases where low frequency illumination is or can be an issue, one may employ holographic or diffractive optical elements to achieve the desired illumination profile, e.g., in rows of lines, grids, or the like.

In particularly preferred aspects, an illumination profile is applied to the signal sources in a linear format, e.g., using a linearized illumination profile or "line illumination", to simultaneously illuminate rows or columns of a plurality of signal sources, while reducing illumination of non-signal source spaces between such rows or columns. Line illumination or a linear illumination profile refers to the illumination of an elongated region or line of a substrate. Typically, the line illumination will typically have a length dimension that is substantially greater than its width dimension, e.g., having an aspect ratio (length:width) of at least 5, preferably greater than 10, more preferably greater than 100.

Figure 13:
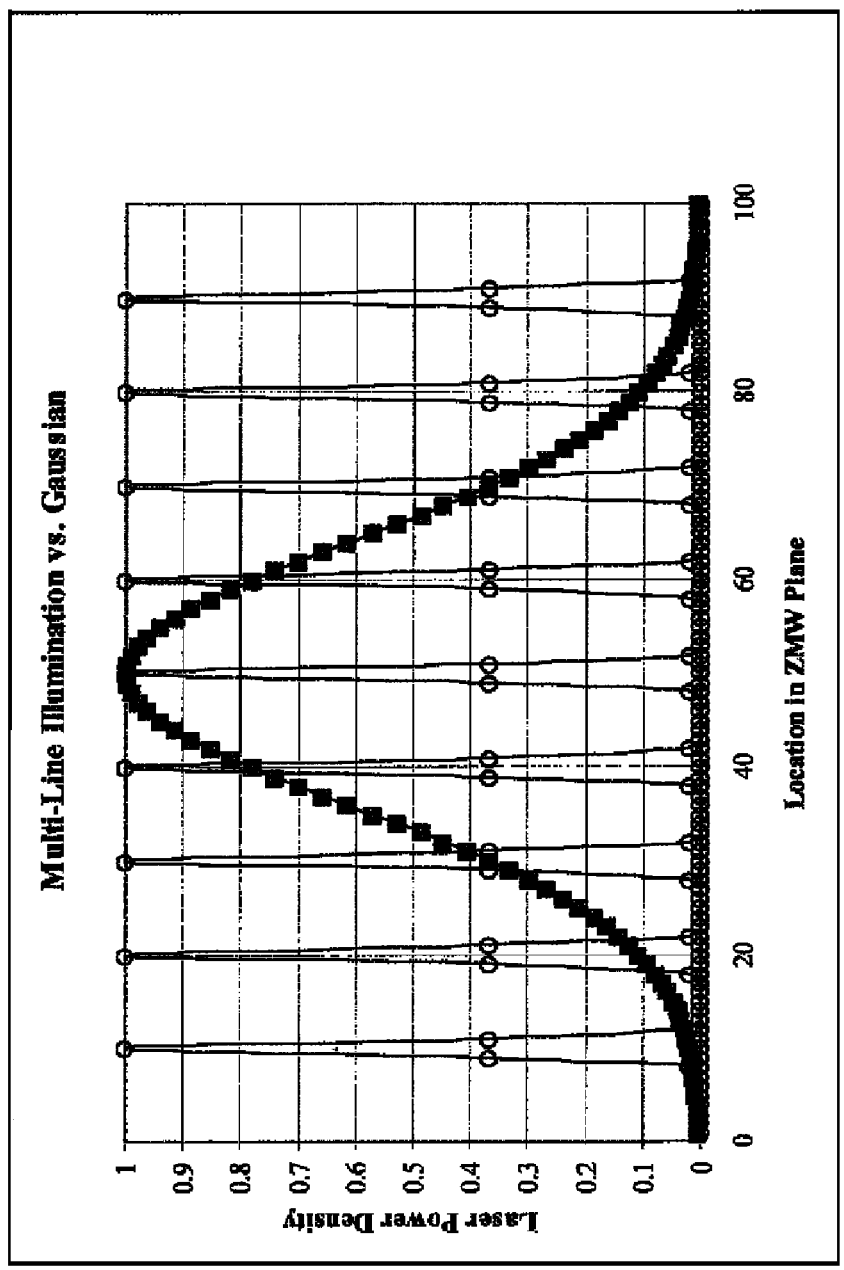
FIG. 13 provides a comparative plot of illumination profiles of flood illumination and multi-line illumination incident upon a substrate.

As will be appreciated, use of line illumination, particularly when combined with beam shaping techniques, e.g., spatial filtering, provides more effectively distributed illumination profiles across larger areas of a substrate than a standard flood illumination profile, and particularly reduces excessive noise contributions associated with illuminating non-relevant portions of a substrate. For example, in the case of systems that direct excitation illumination at the signal source and measure responsive fluorescence, such noise can be a result of reflected excitation radiation that bleeds through the fluorescence collection optics, autofluorescence of the substrate or other illuminated materials, and the like. In addition, by selectively directing the excitation radiation substantially at relevant regions of the substrate, one can effectively reduce the excitation power requirements of the system, improving system costs, and reducing effects of heating and other excessive illumination problems. FIG. 13 provides an illustration of some of the benefits of line illumination as compared to flood illumination. In particular, and as shown, flood illumination provides a power density profile (shown as a broad peak) over the surface of the substrate that varies in a Gaussian distribution that provides substantially lower power to a large proportion of the substrate area, e.g., including a large number of potential signal sources, and provides maximum power at only a very small portion of the substrate (Peak maximum).

A multi-line illumination profile (shown with multiple peaks), on the other hand, provides more even illumination across a broader portion of the substrate area, provides more even illumination to more signal sources, and provides optimal power levels to such signal sources (multiple peak maxima). In addition, by ensuring that the peaks of the line illumination profile correspond to rows or columns of signal sources in an array of signal sources, illumination of substantial portions of irrelevant substrate area would be avoided as compared to flood illumination. As noted elsewhere herein, such irrelevant illumination yields problems of wasted or otherwise problematic illumination power, and excessive noise levels deriving from, e.g., illumination bleed through, autofluorescence, etc. In addition to the foregoing advantages, it will be appreciated that use of a multi-line illumination strategy may be used in conjunction with, or as an alternative to the asymmetrically spaced signal source arrays shown in FIG. 3A. In particular, in addition to, or as an alternative to providing greater inter row spacing of signal sources (as compared to intra-row spacing of signal sources), one may direct illumination at rows that are spaced in this fashion, e.g., regardless of whether additional rows fall between illuminated rows. Again, as noted above, illumination lines may be spaced apart so as to permit resolution of various signal components from each row of signal sources.

In certain preferred aspects, holographic optical elements (HOE), cylindrical lenses or microlenses, or arrays of cylindrical lenses or microlenses are used to modulate the excitation light to provide illumination in a linear profile or format so as to preferentially illuminate regions that include signal sources, and do not illuminate regions of the substrate that include no signal sources. Further, such optical elements may yield excitation illumination profiles on the substrate in multiple lines, i.e., in parallel and/or in orthogonal orientation, e.g., as a grid, or the like. For purposes of discussion, and with reference to direction at the substrate and included arrays of signal sources, the "laser spot" or "excitation radiation spot" refers to any of a variety of different beam shapes, configurations and orientations that are incident upon the substrate, including ellipses, lines, grids, and the like. As will be appreciated, when selectively directing excitation radiation at the signal sources on the substrate, the system may be equipped with certain alignment tools to facilitate alignment of the excitation radiation with the arrays of signal sources on the substrate. Such tools may include reference positions on the substrate that may be identified, either manually or automatically, by the system, to orient and/or focus the system appropriately on the array of signal sources on the substrate.

Figure 6:
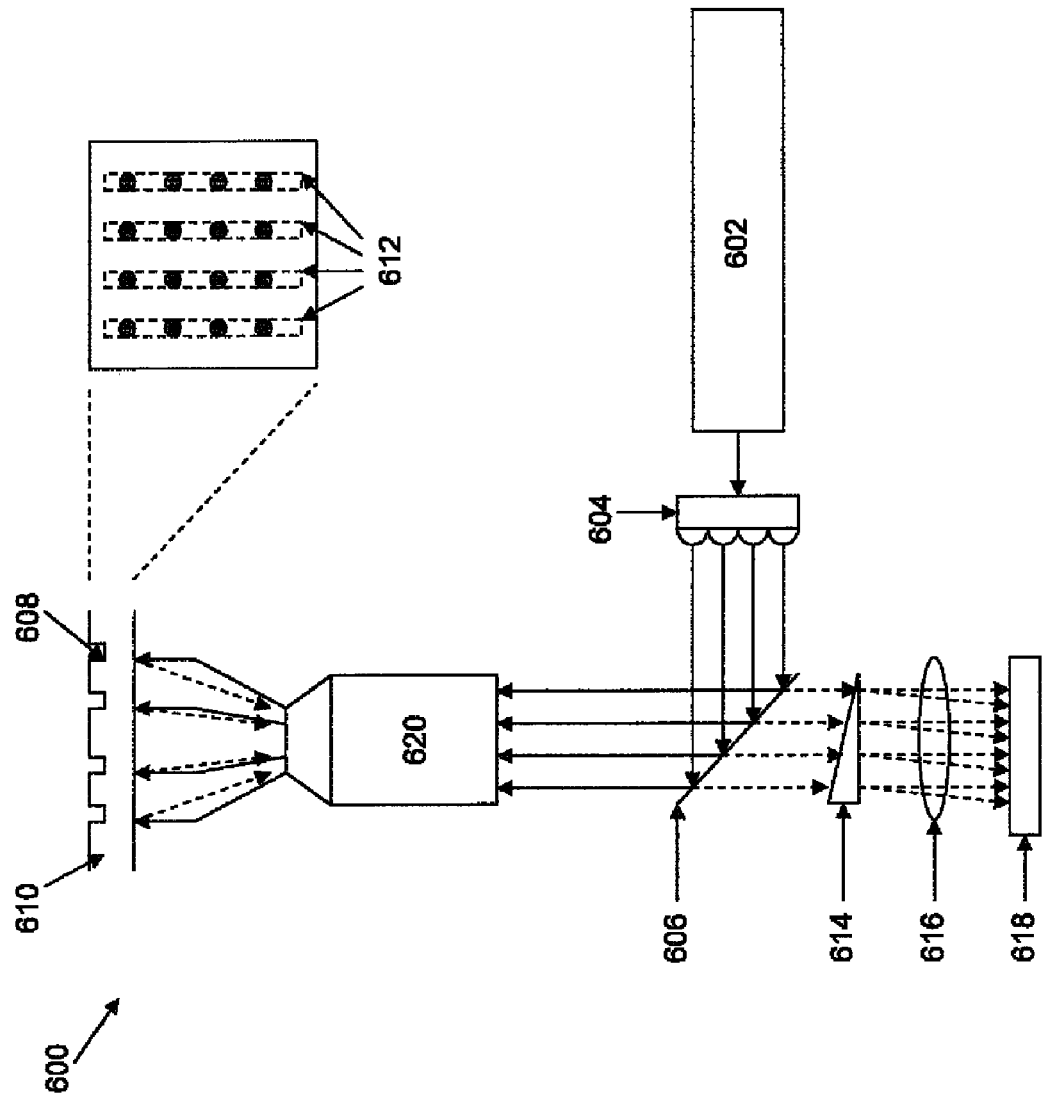
FIG. 6 provides a schematic illustration of a system of the present invention that includes optical componentry for simultaneous illumination of larger numbers of signal sources on the substrates.

A schematic illustration of this aspect of the invention is shown in FIG. 6. As shown, the excitation illumination portion of an overall system 600 includes the excitation light source, e.g., laser 602, that is directed through an appropriate optical element, here shown as beam splitting optical components and/or an array of cylindrical lenses and/or optional imaging lenses (all shown collectively as element 604), to an appropriate dichroic mirror, e.g., dichroic 606, which directs the excitation radiation (shown as solid arrows) up through objective lens 620 and toward substrate 610. As noted previously, the spatial profile of the excitation radiation is configured to preferentially provide greater excitation radiation at the various signal sources 608 on the substrate 610, which is in the focal plane of the objective lens 620. An alternate view of substrate 610 shows the illumination profile as a series of parallel illumination regions on the substrate (as indicated by the dashed outlines 612).

As described elsewhere herein, the emitted fluorescence or other optical signals from the signal sources, are then collected by objective 620, passed through dichroic 606, and are optionally subjected to spectral separation of the signal components, e.g., via prism 614, and ultimately directed to a detector, e.g., detector array 618. In addition to the various optical components already discussed, the optical trains of the systems described herein may also include one or more imaging lenses, e.g., lens 616, to provide a resolved image of the separated, and directed optical signals onto an image plane of, e.g., a detector array 618.

In addition to linearizing an illumination profile, e.g., using a cylindrical lens, it may also be desirable to provide the linearized beam or spot with a more uniform intensity when incident upon the substrate. In particular, in linearizing an illumination spot, one does not eliminate the decrease in intensity at the spot's edges, but merely refocuses those decreases. As such, at the ends of an illumination line, absent additional manipulations, one would expect to see a decrease in light intensity. In accordance with at least one aspect of the invention, the optical train is configured to provide a uniform line illumination profile upon the substrate with tailing edges substantially reduced over a simple linearized spot. In general, this is accomplished by passing the illumination beam through a spatial filter that blocks the edges of the illumination spot that will refocus as the ends of the illumination line. Again, HOEs may be used in controlled beam shaping applications. Alternatively, the spatial filtering may be applied to the linearized beam, rather to the original illumination beam. Other spatial filters may additionally be applied to illumination beams either in place of or in addition to those described herein, including, e.g., confocal pinhole filters, and the like.

Line illumination may be applied to a single row or column of signal sources. However, because arrays of signal sources are typically provided in rows or columns of co-linear sources, it will often be desirable to provide multiple discrete illumination lines to illuminate the various discrete rows or columns while avoiding illuminating the spaces between such rows or columns. Line illumination may be applied on a single row or column basis or it may applied in multiple separate lines to illuminate multiple different rows and/or columns of signal sources. In preferred aspects, for example, one or more lines may be applied in illuminating signal sources, in some cases 2 lines, 4 lines, 10 lines, 20 lines, 50 lines or more may be used to illuminate rows or columns of signal sources.

Multiple illumination lines may be provided by a number of means, including, for example, the use of multiple excitation sources, as described elsewhere herein. However, due to the costs associated with multiple excitation sources such as lasers, the amount of space required for more complex optical trains, and the like, in many cases it is preferable to divide up illumination beams from one or only a few excitation sources.

One approach to providing multiple illumination beams incident upon a substrate is to direct the original beam through a diffractive element, e.g., a grating, to generate multiple illumination beams from a single original beam. While effective at generating multiple illumination beams, diffractive elements generally are not wavelength independent, e.g., different illumination lines will have different spectral characteristics or wavelength ranges. Because many analyses depend upon relatively precise control of excitation wavelengths, in preferred systems, beam division is substantially wavelength independent, e.g., each illumination line will have substantially the same spectral characteristics as the others.

In preferred aspects, the present invention provides a number of different optical trains that provide multiple discrete illumination beams from individual original beams of excitation light, and do so in a cost and space effective and wavelength independent manner.

Figure 7:
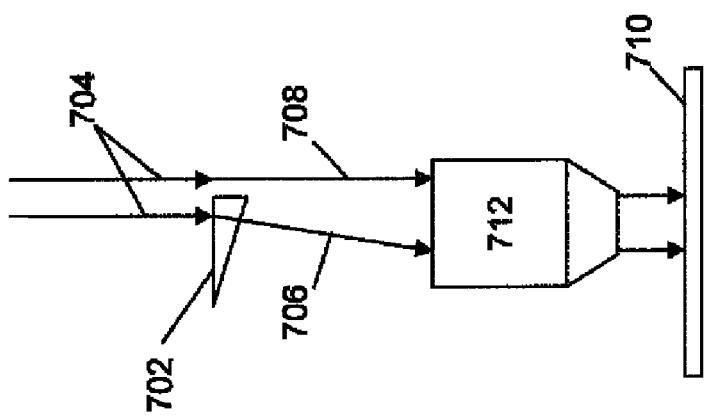
FIG. 7 provides an example of an optical train employing a deflective element in dividing one illumination beam into multiple beams.

In one aspect, the optical train of the system of the invention incorporates a deflective component inserted partially into an individual illumination beam to deflect a portion of that beam and thus create two resulting beams. In one aspect, the deflective component may comprise a prism that is inserted part way, e.g., half wave, into the original laser beam. The portion of the beam passing through the prism is deflected according to the deviation angle of the prism. This approach is schematically illustrated in FIG. 7. As shown, a deflective element such as prism 702 is inserted part way into an original excitation light beam (shown by arrows 704). As a result of a portion of the beam passing through and being deflected by prism 702, the beam is split into two components that diverge by the deflection angle of the prism. The divergent beams (as indicated by arrows 706 and 708) are then directed at different locations on a substrate 710, typically after passing through additional optical elements, such as cylindrical lenses (not shown), objective 712, and the like. The spacing between the two beams, or their linearized spots on the substrate, will typically be related to the deflection angle of the prism and the distance between the prism 702 and objective 712. A variety of different types of deflective elements may be employed in splitting beams in the systems of the invention, including, e.g., prisms, gratings, angled or hinged mirrors, or the like.

Figure 8:
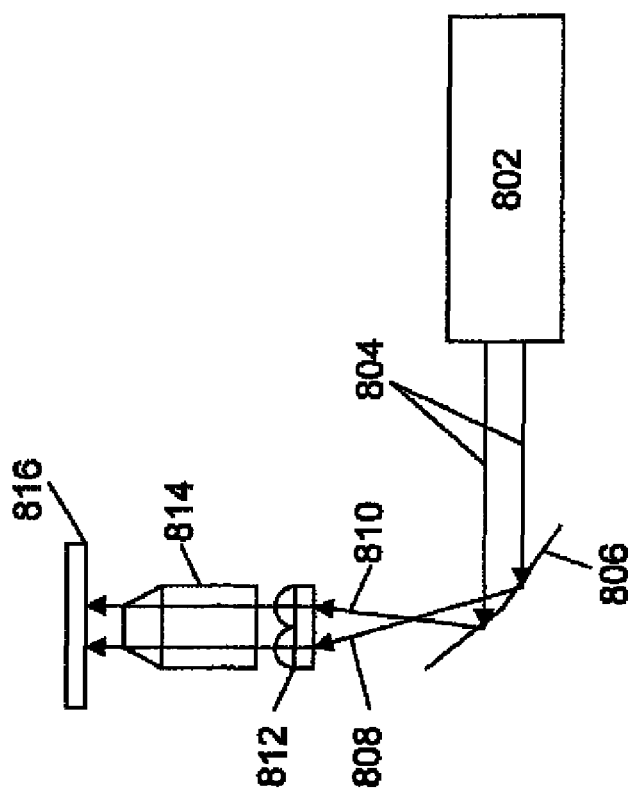
FIG. 8 provides an alternative example of use of a deflective element in dividing illumination beams.

In certain aspects, use of prisms or gratings may be less preferred as they can introduce some wavelength dependence upon the deflection of a portion of the beam which may be problematic for the end application. As such, in an alternative arrangement, a hinged mirror is used as the deflective element to split the original beam into two discrete beams. Because it is a reflective element, it does not introduce any wavelength dependent variations in the deflection of the beam portions. This is schematically illustrated in FIG. 8. As shown, the excitation source, e.g., laser 802, directs original beam (shown by arrows 804) at a hinged mirror 806. The beam is deflected at two divergent angles, resulting in two discrete beams, indicated by arrows 808 and 810. As with the separated beams shown in FIG. 7, the beams are then focused through appropriate optics, e.g., cylindrical lens 812 and objective 814, onto the substrate 816. As will be appreciated, in certain aspects, the hinged mirror may be inserted into the optical train at different places along the optical path, for example, after the cylindrical lens and/or an imaging lens. Again, the separation of the illumination spots or lines on substrate 816 will generally depend upon the angle of deflection of the hinged mirror and the distance between the hinged mirror 806 and the other optical components, e.g., objective 814.

While the use of any of the foregoing deflective elements is effective in providing multiple beams, their use can have limited flexibility in some regards. In particular, as noted above, the spacing between adjacent beams is typically dependent upon the deflection angle of the deflective element and the distance to the substrate. As such, adjustments to this spacing can only be made to all discrete beams, simultaneously, and typically only by either exchanging the deflective element with one having a different angle of deflection, or by adjusting the distance from the objective. In some cases, however, the precision with which individual beams must be directed and variability among substrates or groups of signal sources on a single substrate may dictate a need for adjustability of the positioning of individual beams relative to each other.

Figure 9:
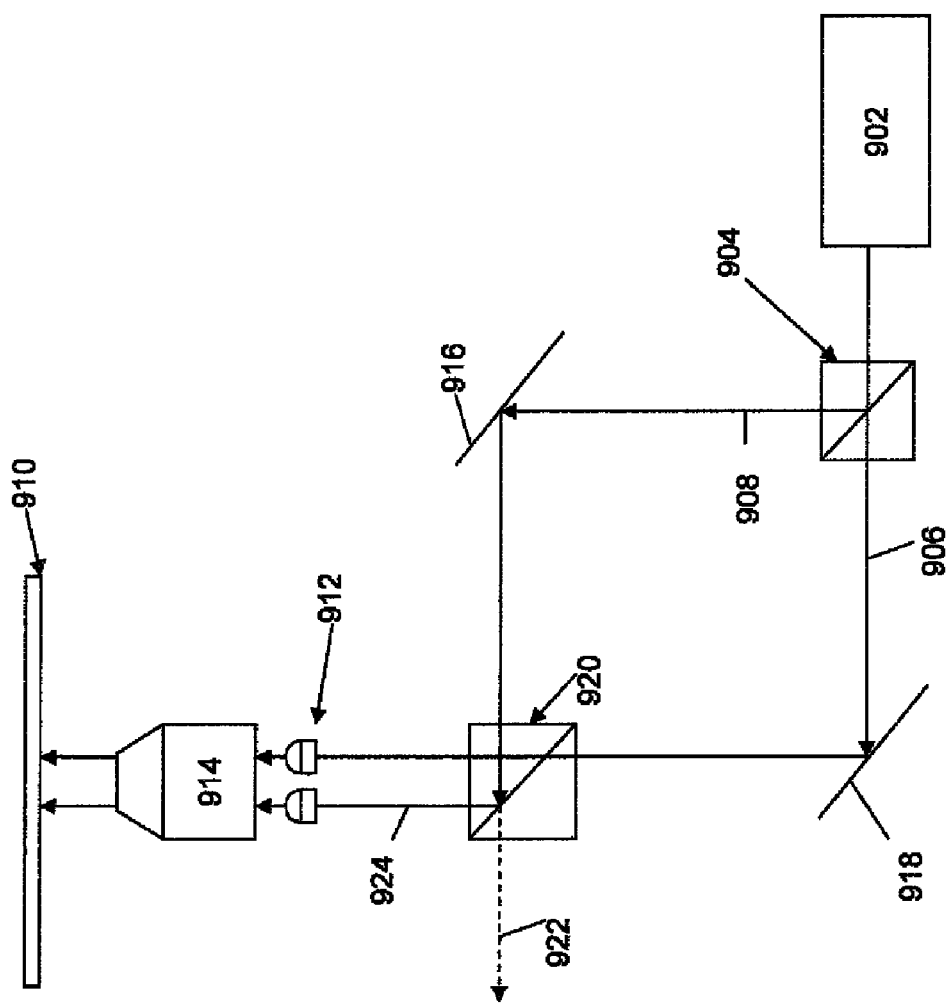
FIG. 9 schematically illustrates an optical train employing conventional beam splitting optics to generate multiple illumination beams for subsequent linearization.

One optical train for accomplishing this is generally illustrated in FIG. 9. As shown, the illumination beam from, e.g., a single excitation source 902 is passed through a beam splitter 904 to produce two illumination beams (indicated by arrows 906 and 908). Depending upon the orientation of the beam splitter, one or both beams are then redirected to provide the illumination beam upon different locations of the substrate 910, after passing through additional optical elements such as objective 914, cylindrical lenses 912, and the like. Redirection may be accomplished using any number of different reflective optics or mirrors, e.g., such as mirrors 916-918. Optionally, an additional partially transmissive reflective element, such as beam splitter 920 may be used to redirect the beams onto closely spaced regions of substrate.

While effective at providing multiple illumination beams upon a substrate, it will be appreciated that the use of standard beam splitters and reflective optics may be difficult to implement for larger scale multiplexing of the system. In particular, the reflective optics required for each separate beam substantially add to the complexity and cost of the optical train of a system that seeks to provide greater numbers of discrete illumination beams, e.g., 2, 4, 8, 10, 20, 40, 50 or more discrete beams, directed at an individual substrate. Additionally, because each of the beams will be substantially identical to each other beam, recombination of beams to direct them at closely spaced regions of a substrate, using a single optical element, such as a beam splitter, will result in substantial losses of applied energy (as only half of the photons from each beam would be directed at the substrate), as shown by arrows 922 and 924 in FIG. 9, above.

Accordingly, in another aspect, beam splitting optics are used that provide more flexibility in adjustment of beam spacing, yield beams having little or no wavelength variation, but which retain sufficient differing characteristics to permit their individual direction, even through common optical elements.

Figure 10:
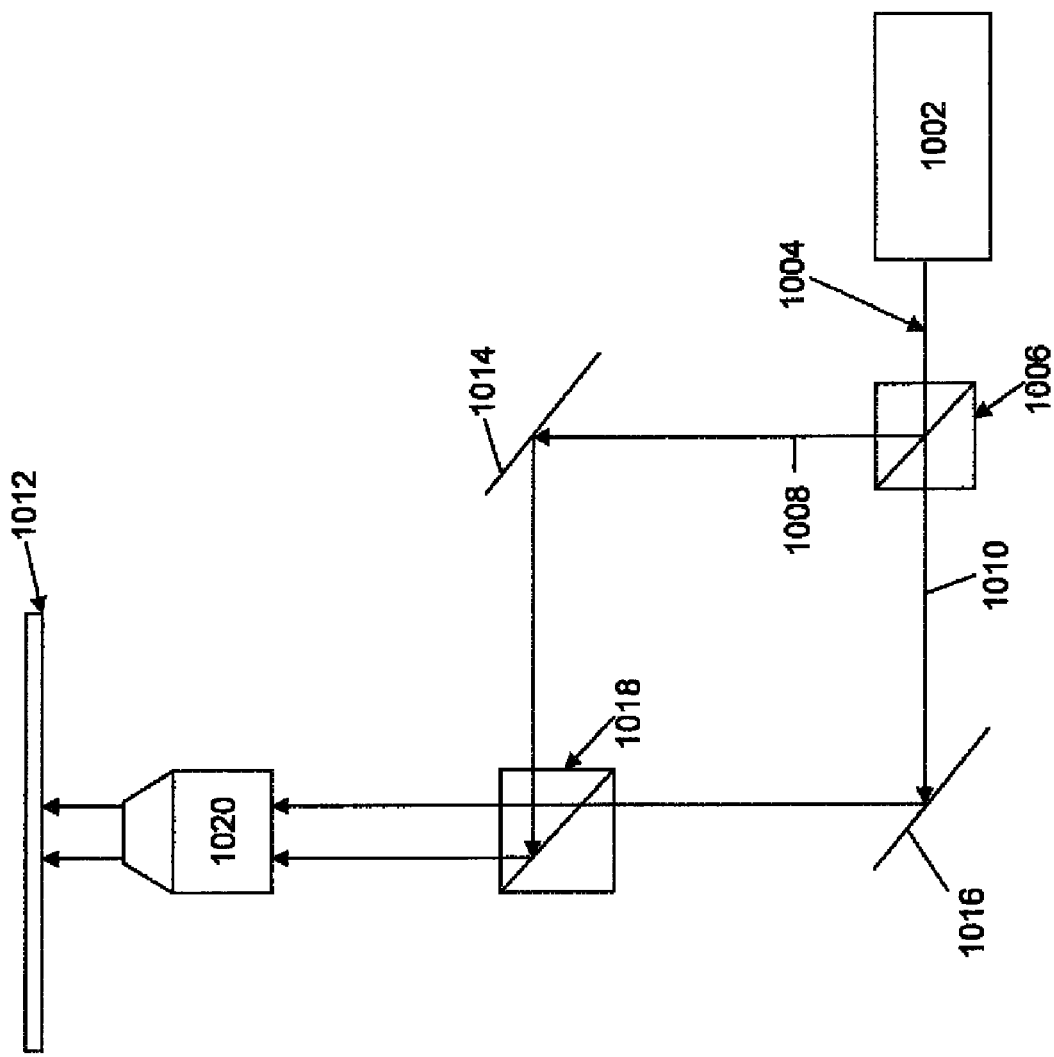
FIG. 10 schematically illustrates an optical train that utilizes polarizing beam splitters in producing multiple illumination beams and/or lines.

For example, in certain preferred aspects, beam division is carried out by splitting beams into their two polar components (s and p components). Each polar component is then separately directed to different locations on the substrate using an independently adjustable optical train. A schematic illustration of this is shown in FIG. 10. As shown, an excitation light source such as laser 1002 directs an original excitation beam (shown by arrow 1004), through a polarizing beam splitter 1006, which separates the original beam into its two polar components, the s-beam 1008 and p-beam 1010. The two discrete beams are each directed to different positions on the substrate 1012, e.g., by reflecting them off of mirrors 1014 and 1016, respectively. By adjusting the positioning and/or angle of one or both of mirrors 1014 and 1016, one can adjust the direction of the beam, and ultimately, the positioning of that beam on the substrate. The two beams are then passed back through a second polarizing beam splitter 1018, which will allow colinearization of the beams, but slightly offset from each other, as a result of the adjusted spacing from one or both of mirrors 1014 and 1016. The offset beams are then passed through objective lens 1020 to be focused upon different locations of substrate 1012. Because the beams are redirected based upon their polarity using polarizing beam splitter 1018, substantially all of the beam is redirected at the substrate, as compared to only a portion of the beam, as shown in FIG. 9, above.

Figure 11:
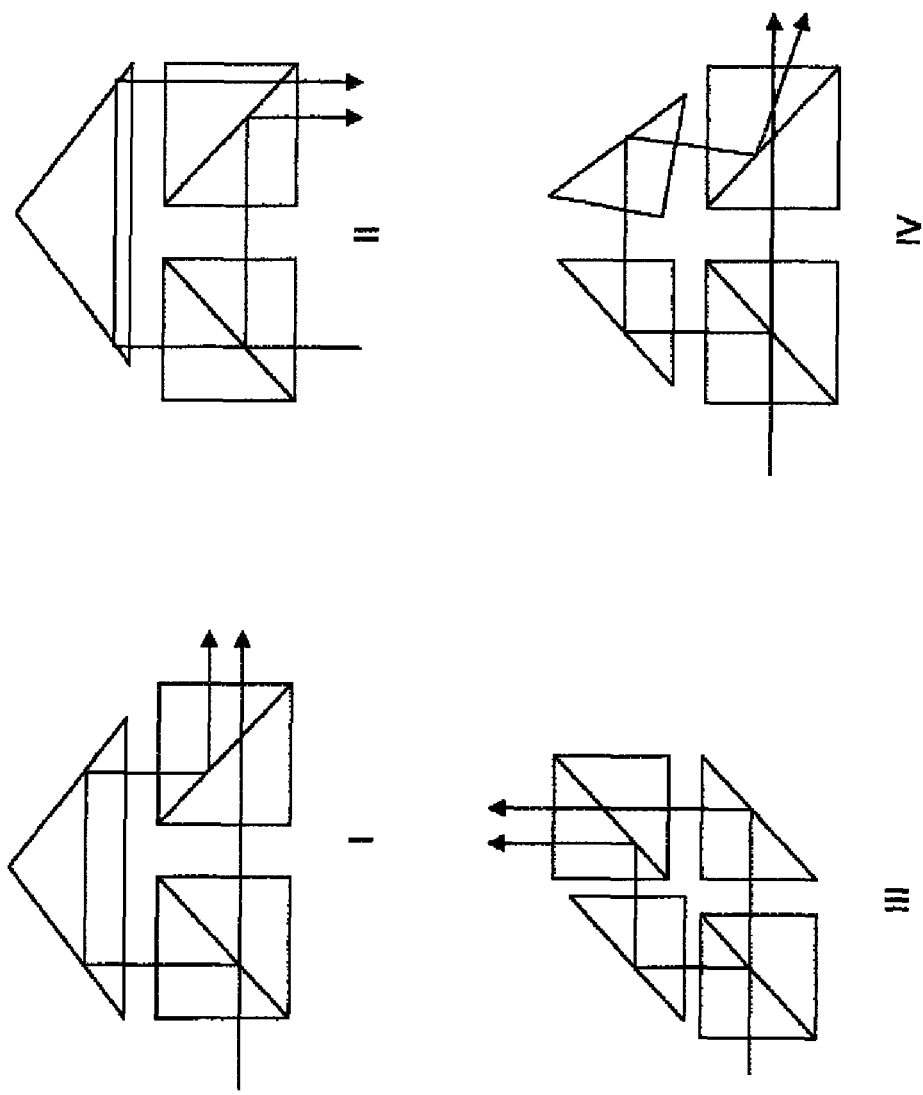
FIG. 11 schematically illustrates a number of alternative optical configurations for splitting and directing different polar beam components of an illumination beam.

A number of variations of the optical train and individual components may be used to accomplish the same goal as shown in FIG. 10. For example, although shown as polarizing beam splitter cubes, it will be appreciated that other polarizing beam splitting mechanisms may be employed. For example, one could employ a pellicle beam splitter in place of a beam splitting cube. Likewise, although shown as employing a particular configuration of optical components in the optical train, it will be appreciated that a number of alternative optical configurations may be used for providing discrete, offset beams from an original beam using a polarizing beam splitter or comparable element, which can be accomplished in differing orientations and/or with different space requirements. Several such configurations are shown in FIG. 11.

Figure 12:
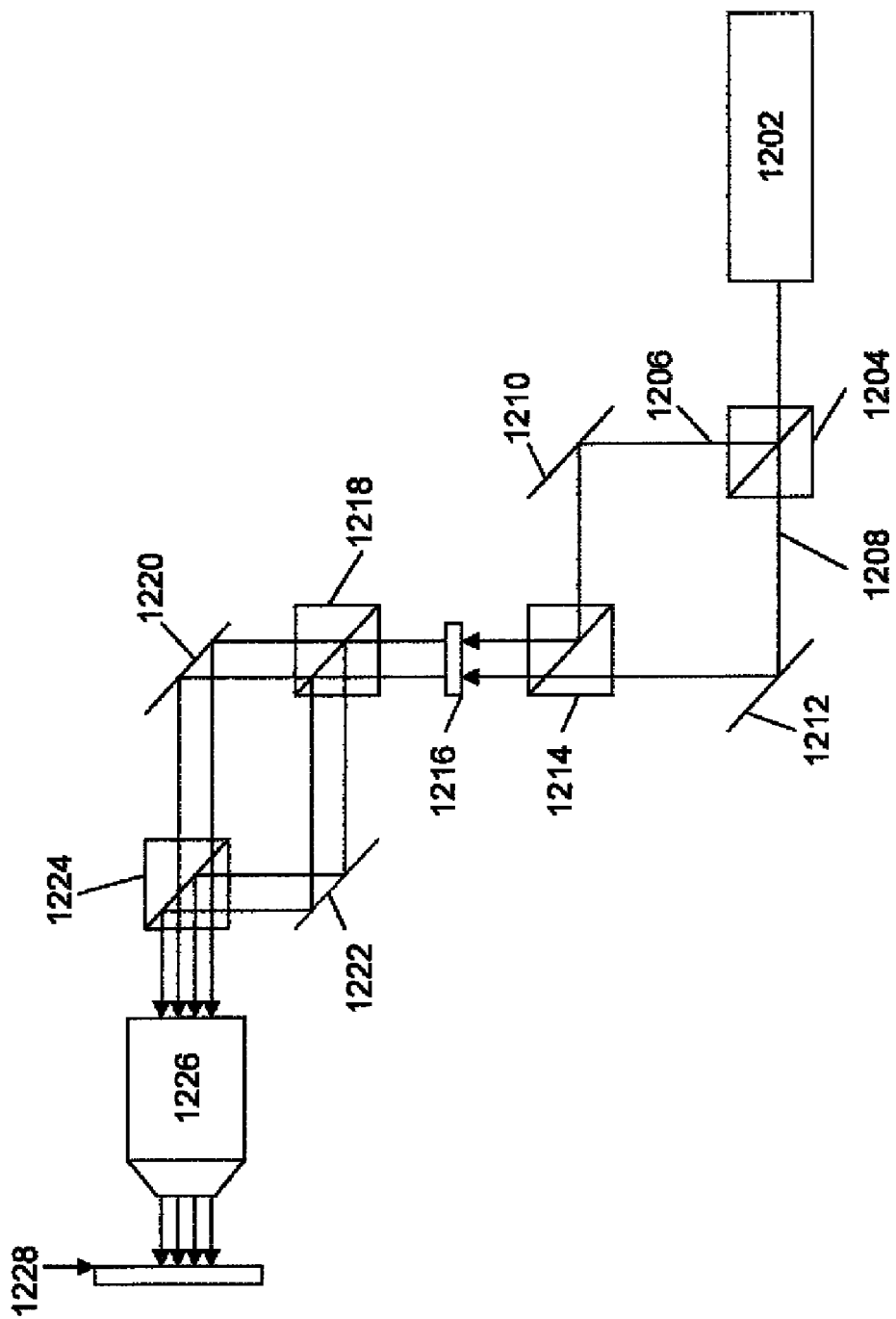
FIG. 12 schematically illustrates an optical train that multiplexes the beam splitting function of the optical trains shown in, e.g., FIGS. 11 and 12.

The foregoing systems may readily be multiplexed by adding in additional beam splitting and adjustment optics to each new beam created. In order to take advantage of additional polarizing beam splitters, it will typically be desirable to insert a half wave plate (e.g., rotated 45° relative to the beam splitting optics) into the optical train the light in each beam, to rotate the polarization of each beam so that it can be further split using polarizing beam splitters, before subjecting it to additional splits/adjustments. A schematic of a multiplexed optics system according to this aspect of the invention is illustrated in FIG. 12. As shown, an excitation light source 1202 again directs a beam of excitation light through polarizing beam splitter 1204 to divide the beam into its polar components (e.g., s-beam 1206 and p-beam 1208). Each beam is then directed through polarizing beam splitter 1214, via mirrors 1210 and 1212, respectively. Beam splitter 1214 serves to bring the beams back together so that they may be commonly directed (e.g., substantially colinearizing or parallelizing the two beams 1206 and 1208) but is positioned to provide a spatial offset between the two beams, or in certain preferred aspects, an offset angle such that the ultimately imaged beams on the substrate are spatially offset. The two polarized beams are then passed through a half wave plate 1216 rotated 45° relative to the orientation of the optical axis of the beam splitting optics, to provide the ability to again split each beam. The two beams are then passed through additional polarizing beam splitter 1218 to further divide each beam into separate polar components, creating 4 beams, which are then brought back together via mirrors 1220 and 1222 and polarizing beam splitter 1224, but positioned so that all four beams, where they are incident upon the substrate, are spatially offset as desired. The four discrete beams are then passed through optical elements, e.g., objective 1226, and focused upon a substrate 1228.

Alternatively, multiplexing may be provided using microlens arrays that include an array of prisms each providing a different deviation angle to the original incident beam, and thus yielding multiple separate beams in one optical component. Similarly, micromirror arrays may be used as multiplexing deflective elements, where each mirror element deflects the incident beam at a different angle to provide multiple separate beams. Again, however, such deflective elements will generally not provide full control over the deflection of individual beams relative to each other. As such, in some cases, it may be desirable to employ MEMS based micromirror arrays, e.g., as found in DLP® systems available from Texas Instruments. Such micromirror arrays provide controlled direction of incident light with relatively high precision, and can produce a range of discrete beams from a single original beam.

The various components of the optical train, e.g., lenses, gratings, filters, prisms, beam splitters, and the like, are generally obtainable commercially from optics suppliers, including, for example, Special Optics, Inc., Newport Corporation, Thorlabs, Inc., CVI Lasers, Lambda Research Optics, Lambda Physics, and Precision Optical, Inc.

In some aspects, the optical train for use in the systems of the present invention utilizes a configuration based upon reflective fluorescence filters that more readily permit implementation of multi-light source, e.g., laser, excitation systems, that may be useful for multi-fluorophore systems, e.g., signal sources that include multiple different fluorophores in generating the signals.

In conventional fluorescence detection schemes, interference filters are typically employed that reflect excitation light at an angle of approximately 90° such that is incident upon the fluorescent sample, and transmit fluorescent light emitted from that sample such that its wave-front remains relatively undisturbed. While the degree of rejected excitation light attainable in such transmissive fluorescence geometries is sufficient for most one or two excitation band applications, these current schemes may not be effectively extended to three or four excitation band schemes, as a single transmissive-fluorescence filter that efficiently passes substantial portions of multiple, e.g., 2, 3, 4 or more, different fluorescent spectra while reflecting the multiple excitation bands, is not readily manufacturable using available technology. Further, while multiple filter components could be combined to achieve this in a multiple laser, multiple emission wavelength system, increased transmission losses, increased optical aberrations, increased size, and increased costs for making higher performance fluorescence transmissive filter systems, make such solutions less desirable.

In contrast, the optical trains of certain preferred configurations of the systems of the invention utilize a reflective fluorescence filter setup in selectively directing emitted light to the detector while blocking excitation light that is reflected from the substrate or other components in the system. In particular, the optical trains of this aspect of the invention typically include at least one optical filter component that reflects emitted fluorescent light from the substrate to direct it to a detector, rather than passing such light. The systems of the invention include a multi-band reflective dichroic filter that selectively reflects multiple emitted fluorescent wavelength ranges, e.g., emitted by multiple different fluorescent materials having distinct emission spectra. In addition to their multi-band reflectivity, these filter components are typically capable of passing excitation light (light at the desired excitation wavelength). As such, the multi-band dichroic are tailored to transmit excitation radiation at multiple different wavelengths, while generally reflecting the longer wavelength emitted fluorescence. The dichroics are further tailored to include relatively narrow reflective ranges, so as to permit transmission of excitation bands that fall between or among two or more emission bands. Such reflective fluorescence systems benefit from superior performance dichroics, as compared to the transmissive dichroics, and also have cost and simplicity benefits.

Because the narrow-band selectivity is applied in reflection versus transmission, more of the reflected excitation radiation is filtered by being transmitted through the multi-band dichroic, and not reflected. To the extent that any excitation radiation is reflected by the multiband dichroic, it can be selectively filtered out following separation of the individual excitation spectra (also referred to as 'color separation'), using an individual narrow-band notch filter that is applied to one separated color (e.g., one selected emission spectrum), as opposed to all colors or emission spectra. Further, fabrication of a single multi-narrow band reflective filter is more readily achievable using available technology than a narrow multi-band transmissive filter.

The optical train included in the systems of the invention also may include an autofocus function for automatically adjusting the objective or other lenses in the optical system to focus the sample material being analyzed within the focal plane of the optical train. A variety of different autofocus systems may generally be incorporated into the systems of the invention.

As alluded to above, one contributor to the noise level produced by a fluorescence based optical analysis system is through the generation of autofluorescence in the system's optical components, e.g., the substrates. One approach for reducing such autofluorescence from the substrates, as set forth above, is to direct excitation radiation at only those portions of the substrate that are relevant to the analysis, e.g., through line or point illumination. In addition to such approaches, one may also reduce autofluorescence of components of the optical train by providing excitation direction through an optical train that differs in whole or in part from the optical train used to collect and direct fluorescent signals to the detector. In particular, by directing the excitation radiation at the substrate through an optical train that does not utilize the same objective lens, filters, focusing optics, etc. as used for the collection and direction of signal components, one can reduce the amount of noise from the system by this autofluorescence component. Additionally, components of the signal direction optical train that are provided to separate excitation radiation from fluorescent signals may be reduced or eliminated, further reducing any noise contribution or signal reduction from these components.

In a first exemplary aspect, excitation radiation is directed at the substrate without passing through the objective lens and or additional optical components of the optical train that collects and transmits fluorescent signals from the substrate. In bypassing the objective lens (and/or other optical components) with the excitation radiation, autofluorescence in such components excited by the excitation radiation is avoided. Differential direction of excitation radiation from collection of optical signals may be accomplished by a variety of mechanisms. By way of example, one may employ a second objective lens positioned to direct the excitation radiation at the signal sources on the substrate. While multiple different objectives may be used, such systems may have limitations in their flexibility. As such, alternative excitation radiation direction schemes may generally be employed.

Figure 16:
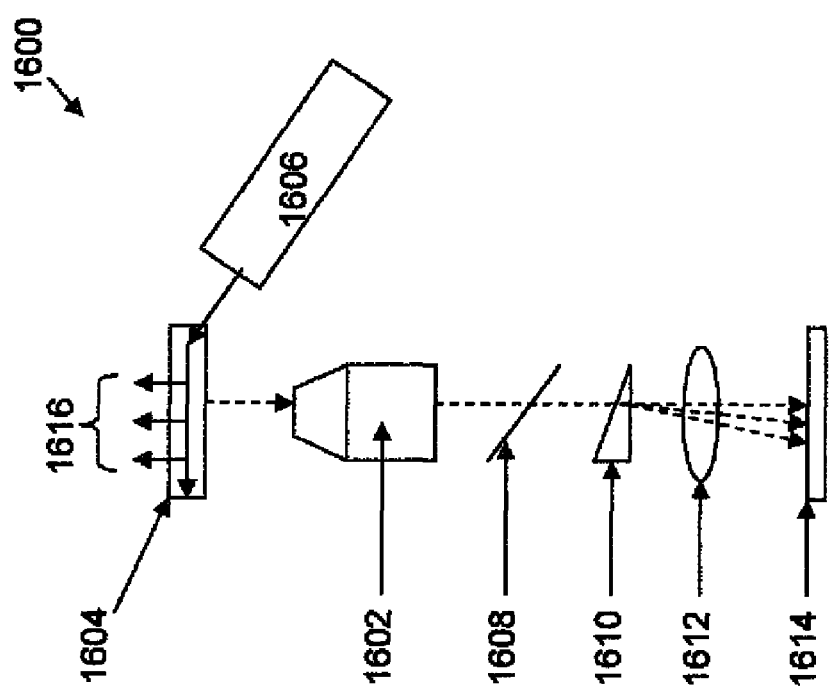
FIG. 16 schematically illustrates a system having an alternate illumination strategy.

In one example, excitation radiation may be directed into and propagated in whole or in part by the substrate itself. As such, one may direct excitation radiation at the substrate from a direction somewhat orthogonal to the direction from which one collects and transmits fluorescent signals, e.g., typically an angle normal to the plane of the substrate. A schematic illustration of such a system is illustrated in FIG. 16. As shown, the optical train set up for collection, transmission and detection of fluorescent signals is similar to that shown in FIG. 5, above. In particular, in the system 1600, the collection optics include objective lens 1602 positioned to receive fluorescent signals from substrate 1604. One or more dichroic filters 1608 may optionally be provided to filter out any extraneous light, e.g., scattered excitation light, that may pass through the objective 1602. The various spectral components of the fluorescent signal are separated, e.g., using prism 1610, and focused through focusing optics, e.g., lens 1612, onto detector 1614. In contrast to the system illustrated in FIG. 5, however, the excitation radiation from the radiation source, e.g., laser 1606, is directed at the substrate not through the collection optics, and particularly not through objective 1602. Instead, the excitation radiation is directed into the substrate 1604 in a manner that presents excitation radiation at the desired signal sources on the substrate 1604, in the desired uniform intensity (shown by arrows 1616).

One mechanism for providing excitation radiation to a plurality of signal sources on the substrate at a desired uniformity involves providing a grating element within the substrate to introduce excitation radiation into and propagate it through or along the substrate to the signal sources. Coupling the illumination radiation with the substrate may be accomplished by any of a variety of mechanisms, including simple lens optics, fiber optics or the like, that direct the illumination to the gratings. The grating may be configured to propagate illumination through the substrate by, e.g., setting up a Plasmon wave along the surface of the substrate, e.g., at the interface of the substrate and another material layer deposited upon that substrate, such as a cladding layer for a zero mode waveguide array. Upon interaction with an opening in the cladding layer, e.g., a zero mode waveguide, the Plasmon wave is coupled into an evanescent field within the zero mode waveguide, thus illuminating a very small volume at the base of the zero mode waveguide. Alternatively, the grating may direct the excitation radiation in a total internal reflection mode using the underlying substrate as a waveguide, where evanescent decay of light at the surface of the substrate provides for illumination of very small volumes at or near that surface, including within any structural confinements on that surface, e.g., zero mode waveguide structures or other spatial confinements. As will be appreciated, propagation of a Plasmon wave along the interface of the substrate and the cladding layer has additional benefits of avoiding substantial autofluorescence of the substrate, as the Plasmon wave penetrates into the substrate only approximately ½ of a wavelength, as opposed to the full thickness of the substrate. Geometry and positioning of gratings can be selected in order to provide uniform excitation intensity over arrays of zero mode waveguides.

As noted elsewhere herein, the optical trains of the invention, whether based upon fluorescence transmission or reflectance, typically directs the emitted, and preferably separated, fluorescent signals to a detector. In particularly preferred aspects, the detector comprises an array of point detectors, such as a diode array detector or a charge coupled device (CCD, ICCD or EMCCD). In the case of such array detectors, it may be desirable for the optical train to provide the directed fluorescence onto the detector in a particular desired configuration. For example, in some cases, it is desirable to image a fluorescent signal onto a plurality of pixels that exceeds a minimum threshold level. For example, providing sufficient signal data from at least 2 pixels, preferably at least 4 pixels, and more preferably at least 10, 20 or even 100 pixels may be desirable to provide for enhanced statistical evaluation of data.

In the case of signals having multiple, separated spectral components, it may be desirable to image each different fluorescent signal component, e.g., each differently colored spot of emitted fluorescence, onto a plurality of pixels of an array detector, so that variations in intensity across an individual signal spot may be accommodated in data analysis, e.g., averaged, discarded, etc. For example, in many cases, each signal component will be imaged on at least two pixels in a detector array, preferably at least 4 or more pixels in the detector array, and in some cases upwards of 10, 20 or 50 or more pixels.

In the case of signal sources, e.g., sample substrates that include an array of discrete signal sources, the total number of pixels involved in detection of a given spectral signal from the overall array will typically vary approximately by the multiple of the sources being analyzed. For example, if each separated color signal from each discrete signal source on an array is imaged onto 4 pixels in the detector array, and 10 signal sources were being analyzed using the same array, then the aggregate signal for that color for the entire array of signal sources would be imaged onto approximately 40 pixels of the detector array. In many cases, as stated elsewhere herein, individual signal components may be imaged upon overlapping pixels in an array and are distinguished based upon other characteristics, e.g., center point, shape, or the like. In such cases, the number of pixels for imaging a number of signal sources will not be a simple multiple of the number of signal components. Notwithstanding the foregoing, the number of pixels required to image a given set of different signals from a signal source will typically be greater than 1 times the number of pixels required to image the signal without color separation, and preferably greater than 2×, 3× or even 4× that of the image size without color separation. As has been reiterated herein, in particularly preferred aspects, the imaged signal will typically include at least two separated spectral components, and preferably 3, 4 or more spectral components that are directed to and imaged upon different detectors or regions on a detector array, utilizing a range of numbers of pixels.

V. Detector

The systems of the invention may generally include any of a variety of different detector types useful for detecting optical signals that are directed to the detector. Examples of different types of detectors include photodiodes, avalanche photodiodes, photomultiplier tubes, imaging detectors, such as charge coupled devices, CMOS (complementary metal oxide semiconductor) sensors or imagers, CCD/CMOS hybrid imagers, and the like. In preferred aspects, imaging detectors are employed in the systems of the invention, so as to provide simultaneous detection over larger areas of the substrates, and consequently, larger numbers of discrete signal sources. Charge coupled device based detectors (CCDs) and CMOS image sensors are particularly preferred for their ability to simultaneously detect and/or monitor signals from large numbers of discrete signal sources on the substrate. Because data derived from the CCDs is assigned to discrete pixels, signals from discrete sources that are incident upon different locations of the CCD may be separately detected and quantified. Further, in applications where relatively high speed, and relatively low signal levels are prevalent, e.g., where the signal sources comprise single molecule type reactions, highly sensitive detectors are generally preferred, such as electron multiplying CCDs (EMCCD) or intensified CCDs (ICCD). Typically, EMCCDs are preferred for their sensitivity to low signal levels.

As with the illumination of signal sources, in preferred aspects, the detection systems in the systems of the invention are typically capable of detecting and/or monitoring signals from at least 2 different signal sources, simultaneously, preferably, at least 10 discrete signal sources, and in many cases, more than 100, more than 1000, and even more than 5000 or more discrete signal sources, simultaneously. Further, the detectors are likewise capable of monitoring or detecting multiple, spatially separated signals or signal components from each such source. In particular, as noted above, signals from each discrete source are preferably spatially separated, at least partially, into at least two, and preferably, three, four or even more separate signal components, that are directed onto the detector array and are capable of resolution and ultimately being separately detected. In some cases, two different signals that may be emitted from a given signal source may not be completely spatially separable onto different regions of a detector array. However, because such signals differ in their emission wavelength spectra, subjecting such different signals to the wavelength separation components of the optical train, e.g., a prism such as prism 610 in FIG. 6, can yield imaged signals on a detector array that have imaged shapes that are characteristic of the particular emission spectrum, while not being completely spatially separable from another signal components having slightly different emission spectra. In such cases, identifying the signal component that gives rise to a detectable event can sometimes include identification of a characteristic shape or center point of an aggregate group of pixels upon which such signal is incident.

VI. Data Management

The systems of the invention also typically include a data processing system coupled to the detector for processing and/or recording signals that are incident upon and detected by the detector, and for processing that data to useful information for the user. For example, in the case of single molecule analyses, e.g., where the signal source comprises fluorogenic reactants, the data processing system may assign a value to the incidence of signal on a given location of the detector at a particular time, as being indicative of the occurrence of a given reaction. The data derived from each signal would typically include one or more of (a) the intensity of the signal, (b) the pixel or pixels upon which the signal was incident, (c) relative time that the signal was detected, and the like. Such data may then be processed to indicate relative rates or activities of reactants, order of reactions, a particular signal source from which the signal was derived, and through knowledge of that source's reactants, the nature of an analyte exposed to such reactants.

For ease of discussion, where the signal source includes template directed DNA synthesis using fluorescent nucleotide analogs and DNA polymerase enzyme within an optical confinement, a signal may be indicative of the incorporation of a nucleotide at a given relative position in the synthesis. Further, using the spectral separation aspects of the optical train, and four different nucleotide analogs all bearing dyes or labels having resolvably different spectral characteristics, e.g., that are separated by the optical train and directed to different locations on the detector (or that possess different imaged shapes) as a result of their differing spectral characteristics, a signal at a given location on the detector (or having a given shape) can be indicative of incorporation of a specific type of analog, and the relative timing of such signal would be indicative that such base occurs in the template sequence before or after another base which gave rise to an earlier or later signal, respectively. Finally, the location on the array where such signals are incident is indicative of the signal source from which the signals derive (e.g., indicating that subsequent signals at the same approximate location (subject to, e.g., spatial separation based upon spectral differences of components of signals from a given source) are likely a result of the continuation of the same reaction). This detection is repeated multiple times to identify the sequence of incorporation of multiple nucleotides. By virtue of the complementarity of incorporation in template directed DNA synthesis, one may then ascertain the underlying sequence of nucleotides in the template sequence.

In addition to the improved ability to separately monitor signals from discrete sources, the use of such CCD or other array detectors provides additional benefits for analysis of signals from the individual signal sources as well as the aggregate signals from the overall array of signal sources. For example, where a signal from a given discrete source is incident upon multiple pixels, the compartmentalization of data on a pixel basis allows selection of optimal pixels in a given imaged signal, for data analysis, e.g., eliminating edge signals that may have higher levels of noise or distortion. Additionally or alternatively, pixels used to obtain signal data for each discrete signal source may be individually tailored for a variety of different purposes, as discussed elsewhere herein. The management of such pixel data is further described in greater detail below.

The systems described herein employ processes that provide more efficient processing of relevant signals. In at least one general aspect, such processes involve the further processing of only relevant signals, while either discarding or combining less relevant signals. In either case, by reducing the amount of signal data that is subjected to the full range of further processing, one can speed up that processing, reduce processing requirements, e.g., computing power, reduce real estate on an array detector required for image data management, extend the lifespan of detector components, and achieve a variety of other benefits. These processes generally may be carried out either in the context of the CCD chip, or they may be performed in a subsequent, off-chip processes, e.g., using a computer. As will be appreciated, in many cases, preferred implementations are carried out within the image data processing steps on the detector array itself.

As alluded to above, in certain aspects, the invention provides for an initial data processing or selection step to avoid the management, storage and/or processing of excessive irrelevant data that is or would be produced by the detection system, as well as the combined processing of certain data from different areas on the detector. In particular, in some cases, one may gain significant advantages, e.g., in terms of speed of data processing and management and usefulness of background signal data, through the selective skipping, removing, or combining of pixel data prior or subsequent to extraction of data, e.g., from a CCD chip. Stated in another way, by ignoring or separately processing data collected from certain pixel areas that do not contain highly relevant data, e.g., they fall outside of a relevant imaged signal, one can speed up the data management process by removing large amounts of irrelevant data from the process or combining into one processible unit, all of the background or less relevant signal data. Additionally, or alternatively, such combined less relevant pixel data may be useful to derive more meaningful background signal levels, or noise, of the system. In either case, the speed and accuracy of the system should benefit.

By way of example, where one is imaging a large number of discrete signal sources or separated signals derived from such sources, on a single detector array, e.g., a CCD, ICCD or EMCCD, space between imaged signals from such discrete sources gives rise to little or no useful data, as it is a "quiet" space. Notwithstanding the lack of useful signal data emanating from these regions of the detector array, the data from such locations has typically been recorded, e.g., as a zero, or some other low level signal value, or other irrelevant value. While such signals can be disregarded as background, their recording and processing to the point of discard still requires memory space for storage and processing capacity for evaluation and ultimate discard. Accordingly, in certain aspects, the invention provides a masking process for filtering out such quiet locations on the detector array, and thus blocking the data from being recorded.

In other aspects, data from related array elements may be combined or "binned" before being subsequently processed, in order to minimize the number of separate data elements that are subject to processing. For example, with reference to the extracted row data described above, each set of rows and/or columns that corresponds to a particular signal source image, or the space between imaged signal sources, may be separately binned for subsequent processing, reducing the number of data elements that are subjected to processing. Similarly, pixels corresponding to images from individual signal source array elements may be binned together and processed. In each of the foregoing cases, whether alone or in combination, the overall number of data elements is substantially reduced over the extraction and processing of each individual pixel element.

In addition to providing benefits of data management selectively binning pixels of imaged signal components may provide advantages of data analysis. For example, when imaging spatially separated signal components, one can selectively bin those elements that are derived from signal rows that are of similar fidelity, allowing subsequent identification of lower fidelity signals, in aggregate. As noted previously, in certain embodiments, the constituent elements of each signal, e.g., the different signal wavelengths emanating from each signal source, are subjected to spatial separation and are imaged onto different pixels, or collections of pixels, on the detector array. As will be appreciated, because constituent signal wavelengths tend to fall over a range rather than within a precise single wavelength or wavelength range in some cases, and because addition of more signal wavelength components within the signal sources as may occur with various applications and/or multiplexing, spatial separation may yield less than complete separation between different signal constituents along each row, e.g., resulting in spectral overlap of the separated signals.

In accordance with certain aspects of the invention, data that is of higher fidelity is processed separately than lower fidelity data, even within an imaged signal. In its simplest sense, only pixels that correspond to the highest fidelity data, e.g., having the highest intensity relative to a noise level of the system, are processed as relevant signals. Other signal components are then subjected to different processing or are discarded. In general, as will be appreciated, such signal components are those that are within the main portion of the imaged signal, e.g., toward the center of the imaged signal, rather than at its periphery.

By binning the lower fidelity data, e.g., that includes excessive levels of mixed signal constituents, one can effectively discard or process all of these signals simultaneously, or at least separately from the relevant pixel data. In accordance with certain aspects of the invention, the data is binned in a manner that combines each set of pixels that includes the same level of spectral overlap (or absence thereof). As with the quiet detector spaces referred to previously, data from the pixels that fall between the pixels having the highest fidelity signals may be processed separately from the high fidelity signal data. For example, it may be discarded prior to subsequent processing, or it may be binned and processed in merely a separate process operation from the high fidelity data. Alternatively, it may be combined with all other low fidelity data, to generate a background level of spectral overlap signal, or the like.

Further, any of these signal data manipulation techniques may be applied dynamically, to optimize different parameters, e.g., signal-to-noise ratio, for each analytical operation that is being performed. In particular, one could adjust the relative spacing of the excluded rows and/or columns, the number of pixels being assigned to each signal event, or any combination of these to achieve a desired signal-to-noise ratio, e.g., by comparing a standard signal to a background noise. Further, this could be performed using appropriate software programming to be able to optimize for any of a number of different regions or numbers of regions or signal sources imaged onto an array.

In some cases, it may be desirable to provide a physical mask over an array detector to filter any signal derived from areas between the signal sources spaces on the detector array to filter out any noise derived from signal in adjoining signal sources/pixel areas. The physical mask may comprise a separate optical element, e.g., an opaque substrate having optical apertures disposed at regions that correspond with the imaged signals, e.g., similar to photolithographic masks used in semiconductor fabrication. Alternatively, the mask may be provided as a layer over the detector array, e.g., using light absorbing polymers or polymers containing light absorbing materials, photoresists, or the like.

As will be appreciated, noise that derives from the system itself, and that will still be present in the event that a mask is used without other adjustments, may be accounted for and dealt with in any of the methods described above. In a further aspect, one could employ detector arrays that are specifically configured, e.g., through the selective placement of detector elements, e.g., pixels in a CCD, to correspond to the regions upon the array where signals will be incident, but with no detector elements where relevant signals will not be incident, and thus exclude some background signal events, e.g., that would otherwise be incident on the array between relevant imaged signal events.

VII. Examples

The following example is illustrative of a number of the benefits of line illumination, as compared to flood illumination, in interrogating a number of arrayed signal sources for fluorescent signals.

Two optical set ups were used to compare flood illumination to linear illumination of zero mode waveguide arrays. A single ZMW array chip was used having inter row spacing of 7.55 µm, with intra-row ZMW spacing of 1.335 µm. The chip was loaded with a 10 µM solution of fluorescent dyes, including Alexa488, Alexa532, Alexa594, and Alexa633, all available from Invitrogen/Molecular Probes (Eugene, Oreg.). The overall optical set up included 488 nm and 633 nm lasers with a 3 mW total laser power at each wavelength, an Olympus 60× air objective, and an EMCCD camera set at a 100 Hz frame rate and an EM gain of 1000×. Flood illumination was achieved by passing the excitation light through a spherical lens (f=250) prior to the objective, while linear illumination was achieved by passing the excitation light through a cylindrical lens (f=130) before the objective. Laser power was adjusted in each case to yield the same laser power density at the ZMW substrate by switching in and out an O.D. 2.0 filter, resulting in 3 mW applied laser power for the 488 nm and 633 nm lasers in the flood illumination set up, and 0.03 mW for the 488 nm and 633 nm lasers, in the linear illumination set up.

For the flood illumination case, the ratio of ZMW fluorescent signal to autofluorescence signal was approximately 1:1, while in the line illumination case, that ratio was approximately 50:1. In addition to the substantially improved optical SNR, the same or similar EMCCD signal levels were achieved in the line illumination case as compared to the flood illumination case, using approximately 1% of the required laser power.

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety for all purposes.

What is claimed is:

1. A method of analyzing a plurality of signal sources on a substrate, comprising:
providing at least first plurality and second plurality of adjacent signal sources on a substrate, wherein the first plurality of signal sources is in a first row, the second plurality of signal sources is in a second row, and the first row and second row are substantially parallel;
selectively directing excitation radiation at the first plurality and second plurality of signal sources while not substantially illuminating space between the first plurality and second plurality of signal sources,
wherein a first linear illumination profile illuminates the first plurality of signal sources, and a second linear illumination profile simultaneously illuminates the second plurality of signal sources, and the distance between the first illumination profile and the second illumination profile corresponds to the distance between the first row and the second row of signal sources.

2. The method of claim 1 wherein the first plurality and second plurality of signal sources comprise chemical or biochemical reactions.

3. The method of claim 2 wherein the chemical or biochemical reactions include immunoassays, enzymatic assays, receptor assays, nucleic acid hybridization assays, nucleic acid synthesis reactions, cellular assays.

4. The method of claim 2 wherein the chemical or biochemical reactions comprise single molecule analysis.

5. The method of claim 2 wherein the chemical or biochemical reactions comprise nucleic acid sequencing reactions.

6. The method of claim 2 wherein the chemical or biochemical reactions result in one or more of the consumption, production and conversion of a material, that is capable of generating an optically detectable signal.

7. The method of claim 1 wherein the signal sources comprise wells, depressions, channels, or other structures that retain reaction constituents.

8. The method of claim 1 wherein the signal sources comprise zones that are maintained discrete from other regions by chemical barriers.

9. The method of claim 1 wherein the substrate comprises an optically transparent layer upon which the signal sources are disposed.

10. The method of claim 1 wherein the signal sources are provided on the substrate in an array format, having more than 10,000 signal sources.

11. The method of claim 10 wherein the signal sources are regularly spaced on the substrate.

12. The method of claim 1 wherein the spacing between the signal sources is from about 0.1 micron to about 10 micron.

13. The method of claim 1 wherein signal sources comprise zero mode waveguides.

14. The method of claim 1 wherein the spacing between the signal sources is from about 0.8 micron to about 3 micron.

15. The method of claim 1 further comprising optically monitoring signals from the first and second signal sources.

16. The method of claim 15 wherein the signals are concurrently optically monitored in real-time.

17. The method of claim 16 wherein the signals are indicative of the reaction or conversion of a chemical, biochemical, or biological reaction.

18. The method of claim 1 wherein the first and second linear profiles are produced using a lens or a holographic optical element (HOE).

19. The method of claim 1 wherein the first and second linear profiles are shaped using a spatial filter.

20. The method of claim 1 wherein the first and second linear profiles have an aspect ratio (length:width) of greater than 100.

* * * * *